(12) United States Patent
Dobak et al.

(10) Patent No.: US 6,241,722 B1
(45) Date of Patent: Jun. 5, 2001

(54) CRYOGENIC DEVICE, SYSTEM AND METHOD OF USING SAME

(75) Inventors: John D. Dobak, Del Mar; Hong Li, San Diego, both of CA (US)

(73) Assignee: Cryogen, Inc., San Diego, CA (US)

( * ) Notice: Subject to any disclaimer, the term of this patent is extended or adjusted under 35 U.S.C. 154(b) by 0 days.

(21) Appl. No.: 09/098,447

(22) Filed: Jun. 17, 1998

(51) Int. Cl.[7] ................................................. A61B 18/18

(52) U.S. Cl. ................................. 606/23; 606/21; 606/20

(58) Field of Search .......................................... 606/20–26

(56) References Cited

U.S. PATENT DOCUMENTS

| | | |
|---|---|---|
| 3,398,738 | 8/1968 | Lamb et al. . |
| 3,827,436 | 8/1974 | Stumpf et al. . |
| 4,207,897 | 6/1980 | Lloyd et al. . |
| 4,275,734 | 6/1981 | Mitchiner . |
| 4,802,475 | 2/1989 | Weshahy . |
| 5,078,713 | 1/1992 | Varney . |
| 5,108,390 | 4/1992 | Potocky et al. . |
| 5,139,496 | 8/1992 | Hed . |
| 5,147,355 | 9/1992 | Friedman et al. . |
| 5,242,441 | 9/1993 | Avitall . |
| 5,263,493 | 11/1993 | Avitall . |
| 5,275,595 | 1/1994 | Dobak, III . |
| 5,281,213 | 1/1994 | Milder et al. . |
| 5,281,215 | 1/1994 | Milder . |
| 5,281,217 | 1/1994 | Edwards et al. . |
| 5,324,286 | 6/1994 | Fowle . |
| 5,400,602 | 3/1995 | Chang et al. . |
| 5,423,807 | 6/1995 | Milder . |
| 5,462,544 | 10/1995 | Saksena et al. . |
| 5,464,404 | 11/1995 | Abela et al. . |
| 5,545,193 | 8/1996 | Fleischman et al. . |
| 5,555,883 | 9/1996 | Avitall . |

(List continued on next page.)

FOREIGN PATENT DOCUMENTS

| | | |
|---|---|---|
| 0624347 | 11/1994 | (EP) . |
| 0655225 | 5/1995 | (EP) . |
| 2447406 | 9/1981 | (FR) . |
| 2482445 | 11/1981 | (FR) . |
| 2094636 | 9/1982 | (GB) . |
| 2226497 | 7/1990 | (GB) . |
| 2244922 | 12/1991 | (GB) . |
| 2283678 | 5/1995 | (GB) . |
| 93/04647 | 3/1993 | (WO) . |
| 95/13025 | 5/1995 | (WO) . |

OTHER PUBLICATIONS

Lawrie et al.,"Transannular Cryoablation of Ventricular Tachycardia", *J. Thorac Cardiovasc Surg.* 1989;98:1030–6.

(List continued on next page.)

*Primary Examiner*—Linda C. M. Dvorak
*Assistant Examiner*—Roy Gibson
(74) *Attorney, Agent, or Firm*—Skjerven Morrill Macpherson LLP

(57) ABSTRACT

The present invention provides a cryogenic device and system for treating biological tissue, which includes at least two media-flow lumens and a media-expansion element for cooling media flowing within the device. A cooling portion of the device is located along a portion of one of the media-flow lumens. The cooling portion is of a construction suitable for good contact with tissue selected for treatment. Preferably, the device and system employ one or more closed media-flow pathways for efficient recycling of the media employed. Preferably, the device and system also employ efficacious heat-exchange relationships between media-flow conduits for optimal cooling. The device and system are particularly designed for the formation of lesions in biological tissue, most particularly, the formation of deep, elongated and continuous lesions in cardiopulmonary tissue. The present invention also provides a method of using the cryogenic device and system in the treatment of biological tissue.

139 Claims, 6 Drawing Sheets

U.S. PATENT DOCUMENTS

| | | |
|---|---|---|
| 5,573,532 | 11/1996 | Chang et al. . |
| 5,575,787 | 11/1996 | Abela et al. . |
| 5,599,295 | 2/1997 | Rosen et al. . |
| 5,624,595 * | 4/1997 | Sato et al. ............................... 252/68 |
| 5,651,785 | 7/1997 | Abela et al. . |
| 5,676,693 | 10/1997 | LaFontaine . |
| 5,688,267 * | 11/1997 | Panescu et al. ........................ 606/41 |
| 5,693,078 | 12/1997 | Desai et al. . |
| 5,697,928 | 12/1997 | Walcott et al. . |
| 5,702,438 | 12/1997 | Avitall . |
| 5,716,353 | 2/1998 | Matsuura et al. . |
| 5,720,775 | 2/1998 | Larnard . |
| 5,730,127 | 3/1998 | Avitall . |
| 5,733,280 | 3/1998 | Avitall . |
| 5,758,505 | 6/1998 | Dobak, III et al. . |
| 5,759,182 | 6/1998 | Varney et al. . |
| 5,787,715 | 8/1998 | Dobak, III et al. . |
| 5,820,580 * | 10/1998 | Edwards et al. ........................ 604/22 |
| 5,899,899 * | 5/1999 | Arless et al. ............................ 606/22 |
| 5,906,612 * | 5/1999 | Chinn ...................................... 606/20 |
| 5,910,104 | 6/1999 | Dobak, III et al. . |
| 5,956,958 | 9/1999 | Dobak, III et al. . |

OTHER PUBLICATIONS

Guiraudon et al., "Surgical Repair of Wolff–Parkinson–White Syndrome: A New Closed–Heart Technique", *The Annals of Thoracic Surgery*, vol. 37, No. 1, Jan. 1984, pp. 67–71.

Vermeulen et al., "Cryosurgery for Ventricular Bigeminy Using a Transaortic Closed Ventricular Approach", *European Heart Journal*, vol. 9, No. 9, Sep. 1988, pp. 979–990.

Bredikis et., "Surgery of Tachyarrhythmia: Intracardiac Closed Heart Cryoablation", PACE, vol. 13, Dec. 1990, Part II, pp. 1980–1984.

Holman et al., "Cardiac Cryosurgery: Effects of Myocardial Temperature on Cryolesion Size", *Surgery* 93 (2):268–272 (Feb. 1983), abstract.

Misaki et al., "Longterm Effects of Cryosurgery in the Sheep Heart", *Cardiovasc Res* 17(2):61–69 (Feb. 1983), abstract.

Sueda et al., "Efficacy of a Simple Lift Atrial Procedure for Chronic Atrial Fibrillation in Mitral Valve Operations", *Ann Thorac Surg* 63(4): 1070–1075 (Apr. 1997), abstract.

Ruffy et al., "Radiofrequency Delivery Through a Cooled Catheter Tip Allows the Creation of Larger Endomyocardial Lesions in the Ovine Heart", *Journal of Cardiovascular Electrophysiology*, vol. 6, No. 12, Dec. 1995, pp. 1089–1096.

Liem, "Progress in Cardiac Arrhythmia Ablation: Potential for Broader Application and Shorter Procedure Time", *Journal of Cardiothoracic and Vascular Anesthesia*, vol. 11, No. 7, Dec. 1997, pp. 895–900.

Patwardhan et al., "Intraoptive Radiofrequency Microbipolar Coagulation to Replace Incisions of Maze III Procedure for Correcting Atrial Fibrillation in Patients with Rheumatic Valvular Disease", *European Journal of Cardio–Thoracic Surgery* 12 (1997) pp. 627–633.

Nath et al., "Biophysics and Pathology of Catheter Energy Delivery Systems", *Progress in Cardiovascular Diseases*, vol. XXXXVII, No. 4, Jan./Feb. 1995, pp. 185–204.

Futterman et al., "Radiofrequency Catheter Ablation for Supraventricular Tachycardias: Part II", *American Journal of Critical Care*, vol. 3, No. 1, Jan. 1994, pp. 77–80.

Schumann et al., "Prophylactic Treatment of Swine with Bretylium for Experimental Cardiac Catheterization", *Laboratory Animal Science*, vol. 43, No. 3, Jun. 1993, pp. 244–246.

Avitall et al., "Physics and Engineering of Transcatheter Cardiac Tissue Ablation", *Journal of the American College of Cardiology*, vol. 22, No. 3, Sep. 1993, pp. 921–932.

Garratt et al., "The Role of Cryosurgery in the Management of Cardiac Arrhythmias", *Clinical Cardiology*, vol. 14, Feb. 1991, pp. 153–159.

Gillette et al., "Transvenous Cryoablation of the Bundle of His", *Pacing and Clinical Electrophysiology*, vol. 14, No. 4, Part 1, Apr. 1991, pp. 504–510.

Garde, "Cryosurgery of Varicose Veins", *J. Dermatol. Surg. Oncol.* 1994; 20:56–58.

Milleret et al., "Cryogenic Sclerosis of the Saphenous Veins in the Cases of the Varicose Reflux in Obese and Elderly Patients", *Phlebologie*, 1981, 34 (4), 601–605, as translated.

Sobel et al., "Development of Cryosurgical Instrument for Removal of Obstructive Atherosclerotic Cores", pp. 295–297, from the Vascular Surgical Services of the Depts of Surgery and Surgical Research, State University of NY, Downstate Medical Center, and the Becton–Dickinson, Co., Rutherford NJ.

Cheatle et al., "Cryostripping the Long and Short Saphenous Veins", *Br. J. Surg.* Oct. 1993, vol. 80, p. 1283.

Milleret, "Varicose Veins Stripping with a Cryo–Probe", one page, *Chirurgie Vasculaire*.

Mikat et al., "Reaction of the Myocardium and Coronary Arteries to Cryosurgery", *Lab Invest* 37 (6):632–641 (Dec. 1977).

"Stop Junctional Arrhythmias Cold" CCS–100 Cardiac Cryosurgical System, two–page brochure of Frigitronics of Shelton, CT, 5/84.

"Problems in Cryosurgery", one–page brochure of Frigitronics, Bridgeport, CT.

Coxeter, "Developments to Watch: The Deep Freeze for Irregular Heartbrats," *Business Week*, No. 3390, Sep. 19, 1994, p. 90.

Chang, Ph.D. et al., "Development of a High–Performance Multiprobe Cryosurgical Device", Biomedical Instrumentation & Technology, vol. 28, No. 5, Sep./Oct. 1994, pp. 383–390.

* cited by examiner

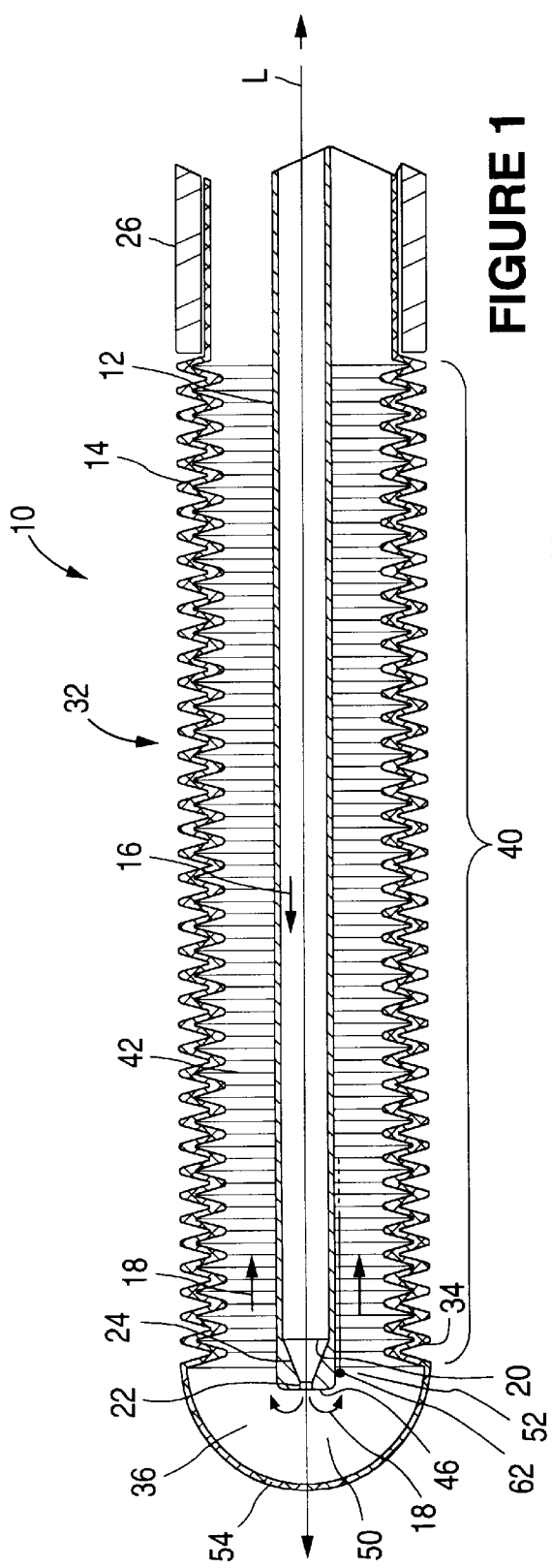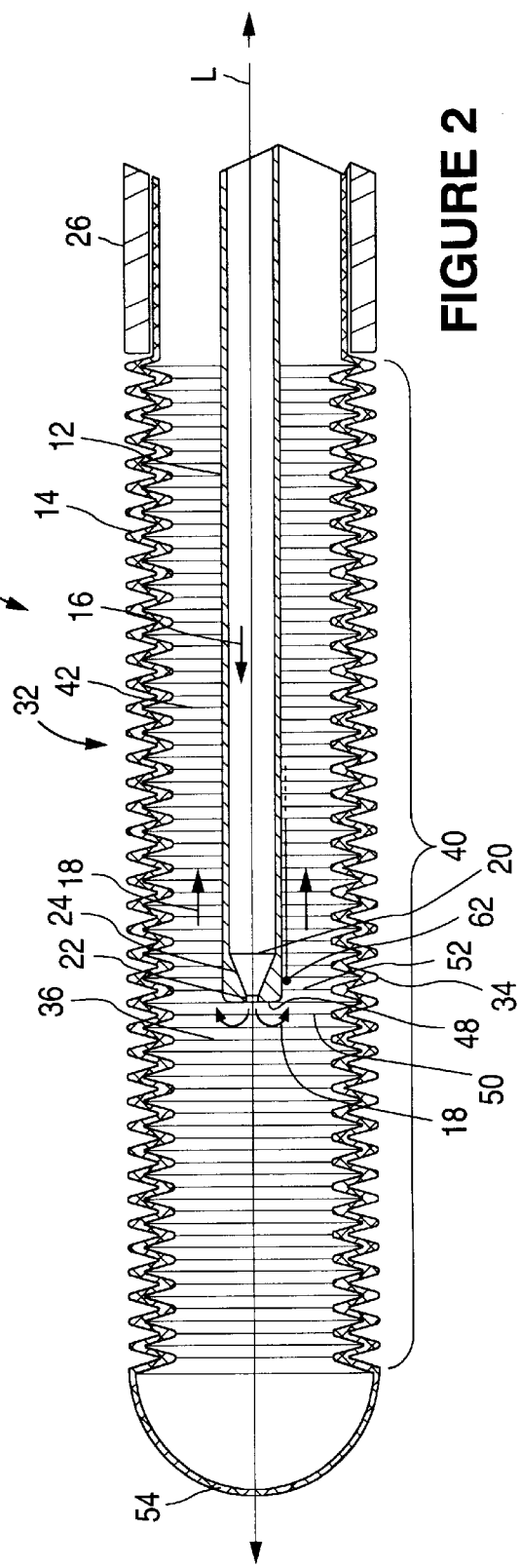

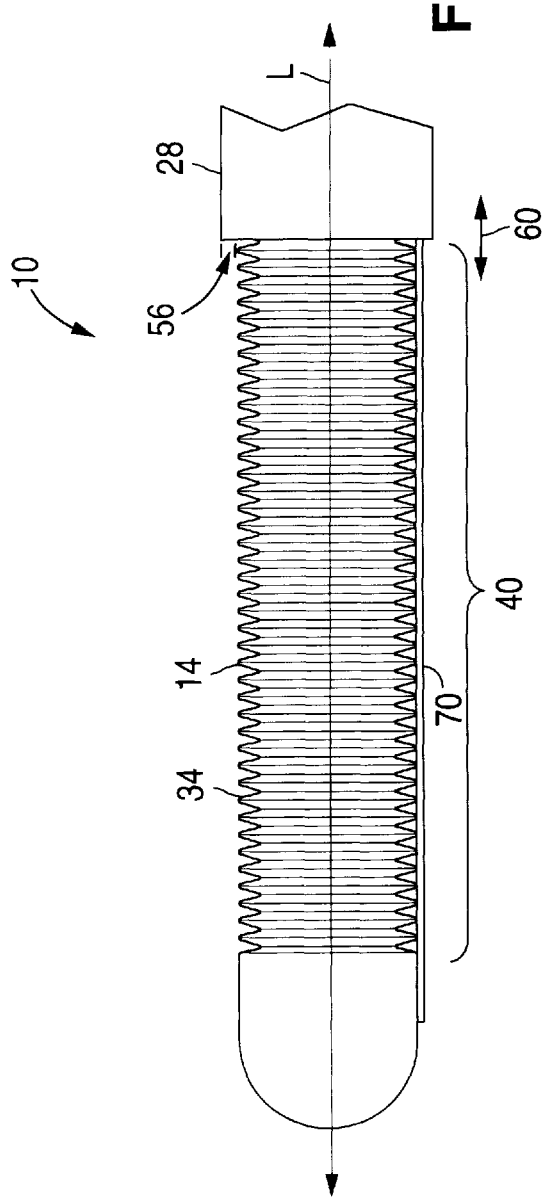
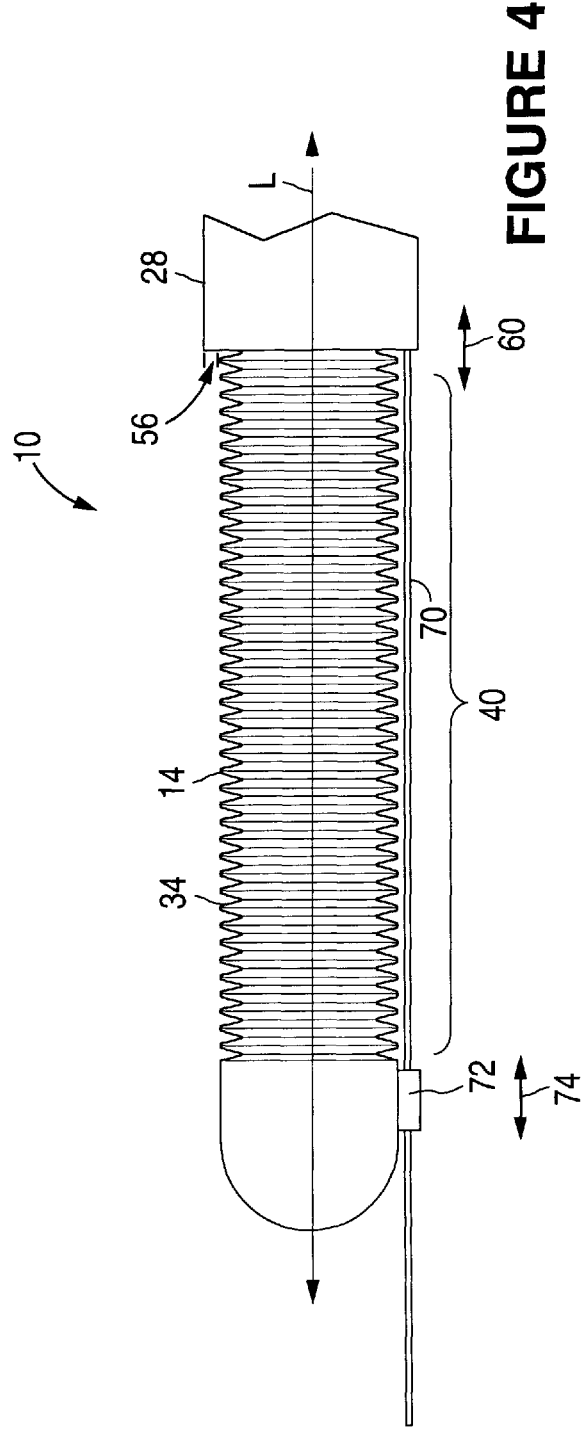

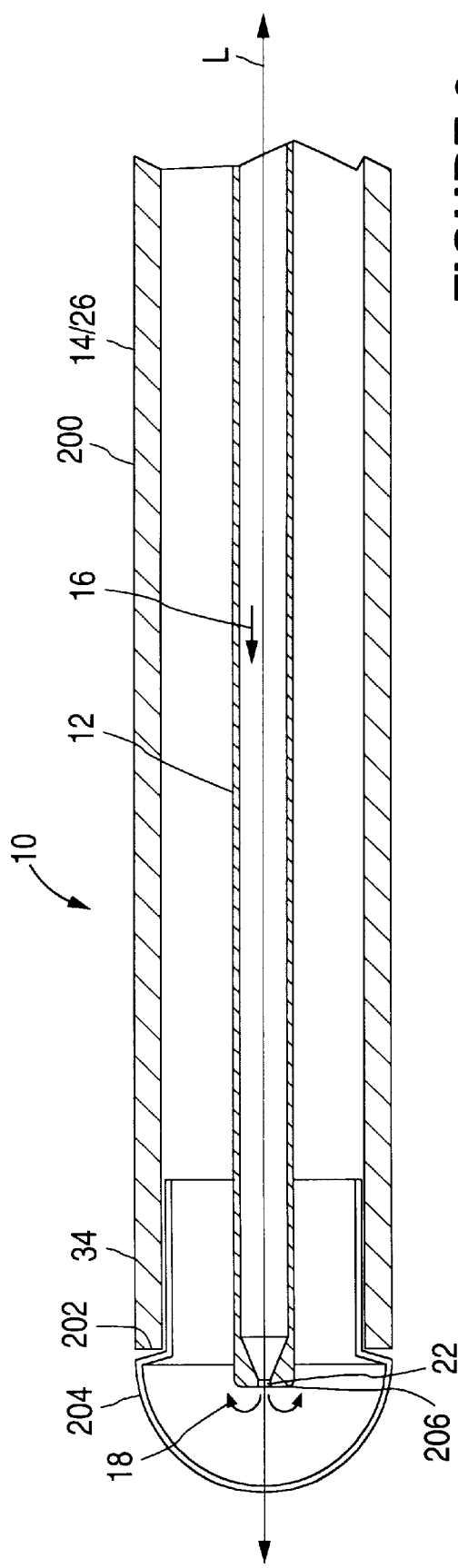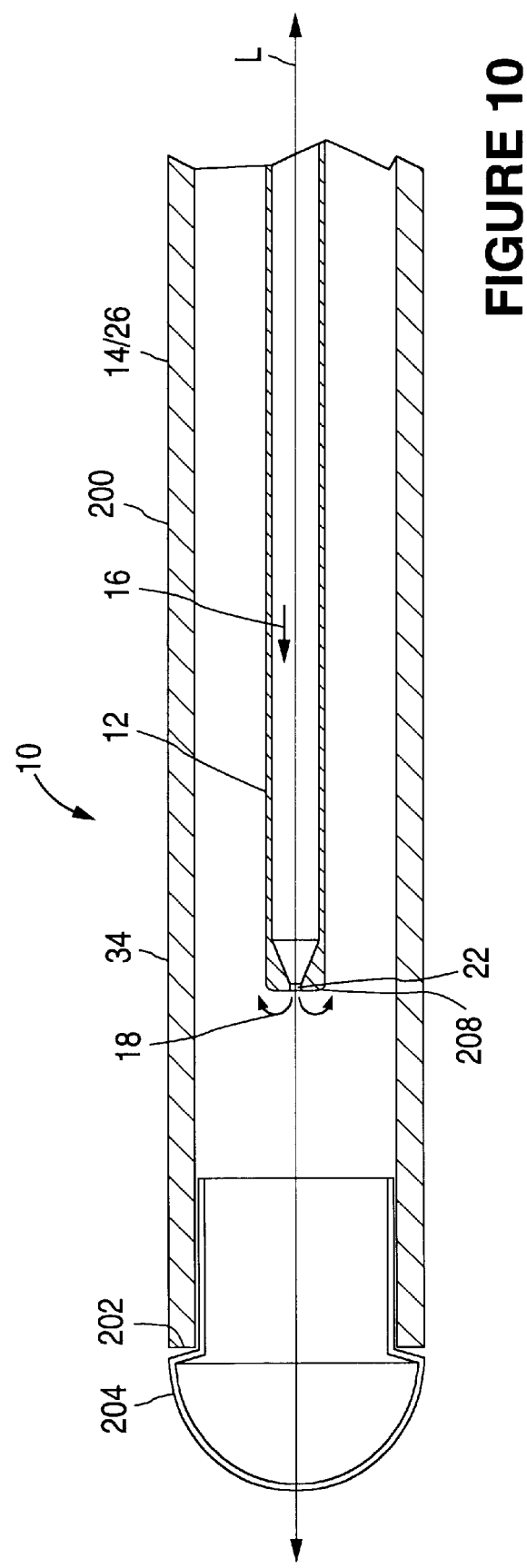

CRYOGENIC DEVICE, SYSTEM AND METHOD OF USING SAME

FIELD OF THE INVENTION

The invention relates generally to a cryogenic catheter and a method of using same. More particularly, this invention relates to a cryogenic catheter which may be used to map cardiopulmonary tissue, and/or to produce lesions in biological tissue. The cryogenic catheter and method of using same are particularly useful in the treatment of tachycardia.

BACKGROUND OF THE INVENTION

Catheters which include a variety of electrode means for the ablation of biological tissue are known. For example, most of the catheters used for the ablation of cardiac tissue employ electrodes which are energized by a radio-frequency ("RF") electrical current. That is, the cardiac tissue is heated by the RF-energized electrodes until a lesion is formed in the desired location. Generally, the RF-electrode catheters are also used to map, or to record, the electrical conduction pathways of the cardiac tissue.

Examples of such RF-energized electrode catheters for use in the treatment of cardiac arrhythmia appear in U.S. Pat. No. 5,720,775 to Larnard; U.S. 5,676,693 to LaFontaine; U.S. Pat. No. 5,555,883 to Avitall; U.S. Pat. No. 5,545,193 to Fleischman et al.; U.S. Pat, No. 5,281,213 to Milder et al.; and U.S. Pat. No. 5,281,215 to Milder.

Generally, in the treatment of tachycardia, electrode mapping is used to locate the originating site of the disturbance in the electrical activity or rhythm of the heart. A focal lesion is formed at the originating site of the arrhythmia to interrupt the abnormal electrical activity. Generally, in the treatment of atrial fibrillation, electrode mapping is used to record the electrical conduction system of the atria in order to ensure that the ablation electrode does not reach the normal conduction system. In such treatment, elongated, continuous lesions are formed in the atrial tissue to block reentry circuits which disrupt the normal electrical activity of the atria.

Use of RF-energized electrode catheters to form such cardiac lesions has significant disadvantages. For example, often when using such a catheter to form a cardiac lesion, the cardiac tissue becomes charred from the RF-energized heating of the tissue, blood in the vicinity of the cardiac tissue undergoing treatment becomes coagulated, and the cardiac tissue undergoes separation and/or popping. Further, it is often difficult to form an effective lesion having sufficient length, continuity and/or depth to interrupt or to block electrical conduction across the lesion, when using an RF-energized electrode catheter.

Theoretical consideration and experimental testing have indicated that the formation of cardiac lesions by cryogenic means overcomes many of the disadvantages associated with the use of RF-energized electrode catheters. Yet, cryogenic means have not become the means of choice, for lack of development of a desirable and effective cryogenic system and technique for the treatment of cardiac conditions.

By way of example, Milder (above) discloses a cryogenic catheter for performing "ice-mapping" and cryogenic ablation of cardiac tissue. The catheter is designed for cryoablation at its tip, such that focal lesions are formed. The catheter of Milder is not suitable for the formation of the elongated, continuous, and/or deep lesions that are desirable in the treatment of various cardiac conditions, such as atrial fibrillation.

There is a need for a cryogenic system, and a method of using same, that provides for efficacious treatment of biological tissue by forming an efficacious lesion in the tissue. There is a particular need for same for the treatment of abnormal conditions in cardiopulmonary tissue.

SUMMARY OF THE INVENTION

According to a primary aspect of the present invention, briefly and generally, a cryogenic device for treating biological tissue is provided, which includes at least two media-flow lumens and a media-expansion element for cooling media flowing within the device. The device is particularly adapted, and/or adaptable, to the tissue being treated, such that good contact between a cooling portion of the device and the tissue is achieved. For example, according to one embodiment, the cooling portion is located along a bellows portion of one of the media-flow lumens, which bellows portion is of a fixed or selectable shape or dimension, suitable for good contact with the selected tissue. In this manner, the device is capable of contacting tissue that is difficult to access, is of a complicated shape and/or of a small size, for the desired treatment of the tissue.

The device may be employed in the treatment of a variety of tissue, such as tissue affected with an undesirable condition, whether benign or malignant, tissue of an organ, and particularly, tissue within a body which is accessible via percutaneous or intravenous means. The device is especially suitable for the treatment of cardiopulmonary tissue, as it may be employed to effect not only deep focal lesions, but also elongated, continuous and/or deep lesions that may be desirable in the treatment of such tissue.

In the device of the present invention, a medium flowing in a first lumen thereof is pressurized and at a first temperature just distal of the expansion element. Upon passage through the expansion element, the medium now flowing into a second lumen is comparatively of a lower pressure and temperature. This cooled medium is sufficient for cooling the tissue when the second lumen is appropriately placed in relation to the tissue.

According to a preferred embodiment of the present invention, the second lumen includes a bellows portion for contacting the tissue and a cooling portion along the bellows portion for cooling the tissue. The bellows portion is constructed to facilitate contact between the cooling portion, or contact portion, of the device and the tissue. To this end, the bellows portion may be longitudinally fixed, or longitudinally expandable or contractible. In a preferred embodiment, at least the contact portion is composed of a super-elastic metal alloy, such as nitinol, which has desirable flexibility, strength and longevity. Given these desirable properties, the entire bellows portion may be composed of this material.

According to one aspect of the present invention, the expansion means is a media-flow restriction means, preferably, an orifice sufficient for Joule-Thomson expansion of the medium flowing therethrough. Preferably, the expansion means is longitudinally moveable so that the contact portion can be moved to a desirable longitudinal position along the bellows portion for optimal cooling of the selected tissue.

The device of the present invention may be advantageously employed over an operating temperature range of from about normal body temperature, for example, when the device is being placed in contact with the tissue, to a desirable cooling temperature. For example, the cooling temperature at the contact portion may be at less than or equal to about 0° C. for adhesion of the contact portion to the selected tissue. Further by way of example, the cooling temperature may be at about −10° C. for the cold-mapping of cardiopulmonary tissue. This cooling temperature may be lower, generally, from about −20° C. to about −150° C., and preferably, from about −70° C. to about −120° C., for forming an efficacious lesion in biological tissue, such as cardiopulmonary tissue.

According to a particular aspect of the invention, the medium supplied to the first lumen may be pre-cooled so that it is at a desirably low temperature before it reaches the expansion means for further cooling. That is, a conduit having a pre-cooling medium flowing therethrough may be disposed in an efficacious heat-exchange relationship with the first lumen to pre-cool the medium flowing in the first lumen. According to yet another aspect of the invention, the second lumen may be in an efficacious heat-exchange relationship with the first lumen for further cooling of the medium flowing in the first lumen. With such heat-exchange relationships, the device can achieve a very low cooling temperature. Further, the pre-cooling and cooling media may be selected to achieve, efficaciously, the cooling desired.

According to another embodiment of the invention, a lumen portion of approximately uniform diameter replaces the bellows portion of the preferred embodiment. In this embodiment, the lumen portion is of a predetermined length, while the expansion means is longitudinally moveable therein so that the cooling portion can be moved to a desirable longitudinal position along the tubular portion for optimal cooling of the selected tissue.

Surprisingly, the advantages of the present invention, such as extreme cooling, may be achieved using a device of small dimensions. Thus, the device is particularly suited to treating biological tissue that may be difficult or impossible to access with larger devices. The overall system, including media sources, compressors, heat-exchange means, and the like, may also be relatively compact and portable for ease of use. Preferably, the media-flow pathways employed in the system are closed, such that the media are efficiently recycled, as opposed to being exhausted from the system.

In use, the cooling or contact portion of the device is placed in contact with a selected portion of tissue, optionally via guiding means, and the medium flowing therethrough is expanded to reach a cooling temperature appropriate for the desired cooling of the tissue. Preferably, the medium is cooled to a temperature sufficient for cooling the tissue to form an efficacious lesion, such as a deep, elongated and continuous lesion, in the tissue. Thus, the device, system and method of the present invention are particularly suited to the treatment of cardiopulmonary tissue, such as cardiopulmonary tissue affected by atrial fibrillation.

Additional objects, advantages and features of the present invention will become apparent from the description of preferred embodiments, set forth below, which should be taken in conjunction with the accompanying drawings, a brief description of which follows.

BRIEF DESCRIPTION OF THE DRAWINGS

FIGS. 1 and 2 are side-elevational views of a device for cooling biological tissue which includes at least two lumens and an expansion element, said device shown in longitudinal cross-section, according to embodiments of the present invention.

FIGS. 3 and 4 are side-elevational views of a device, similar to that shown in FIG. 1 or FIG. 2, which includes guiding means, according to additional embodiments of the present invention.

FIGS. 9 and 10 are side-elevational views of a device for cooling biological tissue which includes at least two lumens and an expansion element, said device shown in longitudinal cross-section, according to embodiments of the present invention.

DESCRIPTION OF PREFERRED EMBODIMENTS

Figure 5:
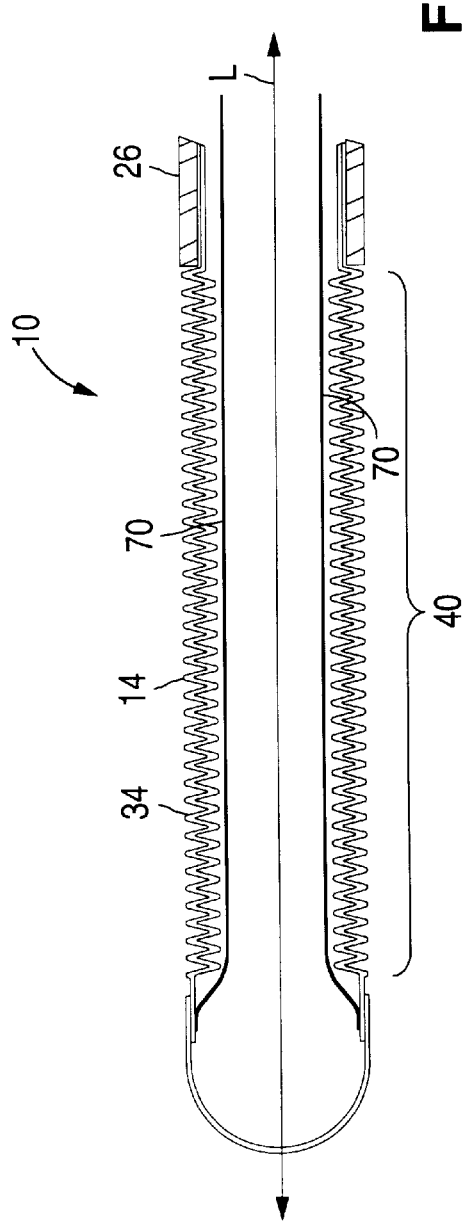
FIG. 5 is a side-elevational view of a device, such as that shown in FIG. 1 or FIG. 2, shown in longitudinal cross-section, which includes guiding means, according to another embodiment of the present invention.

A device 10 for cooling biological tissue which includes a first lumen 12 for passage of a first medium therethrough, and a second lumen 14, which includes a bellows portion 40, for passage of a second medium therethrough, is shown in FIG. 1. Generally, the device extends along a longitudinal axis L, proximal and distal portions of which are shown at the right-most and left-most portions of FIG. 1, respectively.

In this description of preferred embodiments, unless otherwise understood or specified, the terms "proximal" and "distal" are used to refer to relative locations (as above) substantially along or parallel to longitudinal axis L; and the term "longitudinal" is used to refer to a direction substantially along or parallel to longitudinal axis L. Further, reference letters and numerals are used in the drawings and in this description to refer to like features shown or described, unless otherwise understood or specified. These conventions are adopted merely by way of convenience, not by way of limitation.

In device 10, the substantially longitudinal direction of flow of the first medium in the first lumen and the second medium in the second lumen are represented by arrows 16 and 18, respectively. The first medium is a pressurized fluid, which is composed of at least one gas, at least one liquid, or any combination thereof. At a distal portion 20 of the first lumen, the first medium is substantially liquid, or neither substantially gaseous nor substantially liquid, but in a state therebetween. Additionally, the first medium is of a first temperature at a distal portion 20 of the first lumen. Whatever the state of the first medium, its pressure and first temperature at the distal portion are generally in a range of from about 100 psig to about 400 psig and from about 13° C. to about −80° C., respectively, and preferably in a range of from about 150 psig to about 200 psig and from about −35° C. to about −45° C., respectively.

As shown in FIG. 1, the device 10 further includes means 22 for expanding the first medium. Generally, the means for expanding allows for a media pressure drop thereacross. Examples of means for expanding the first medium include media-flow restriction means, such as a lumen 24 (tapered, as shown, or untapered) which is smaller, for example, of lesser diameter, than the first lumen 12; a lumen made of porous material, such that the open spaces therein trap a portion of media, thereby restricting media flow thereacross; preferably, an expansion orifice, such as an orifice 22 suitable for Joule-Thomson expansion of the first medium passing therethrough, as further described herein; and any combination thereof. As shown in FIG. 1, the expanding means 22 is disposed distally relative to the distal portion 20 of the first lumen 12. As further shown, the expanding means may include an elongated portion 24 proximal of the expansion orifice 22. The expanding means is operably connected to the first lumen, for example, attached thereto or an integral part thereof.

An example of a suitable expanding means for use herein is that described in co-pending U.S. patent application Ser. No. 09/075,374 of John D. Dobak, III, et al., filed on May 7, 1998, entitled "PRECOOLING SYSTEM FOR JOULE-THOMSON PROBE", which is a continuation-in-part of prior co-pending applications U.S. patent application Ser. Nos. 08/726,770, filed Oct. 7, 1996, 08/698,044, filed Aug. 15, 1996, and 08/542,123, filed Oct. 12, 1995, and also claims priority from U.S. Provisional patent application Ser. No. 60/054,168, filed Jul. 30, 1997, all of which are incorporated herein in their entireties by this reference. Merely by way of convenience, these applications will be collectively referred to hereinafter as the "John D. Dobak, III, et al. Applications".

When the first medium flows through the expanding means 22, it becomes the second medium which flows in the second lumen 14. That is, the second medium flows into a distal portion 36 of the second lumen which is disposed distally relative to the expanding means and further into a portion 42 of the second lumen 14 which surrounds the first lumen, as indicated by directional arrows 18. Just distal of the expanding means 22, the second medium is of a temperature which is less than the first temperature of the first medium by virtue of media expansion. This second medium is used to cool the tissue when the second lumen 14 is placed in contact with the tissue, as further described herein.

Figure 6:
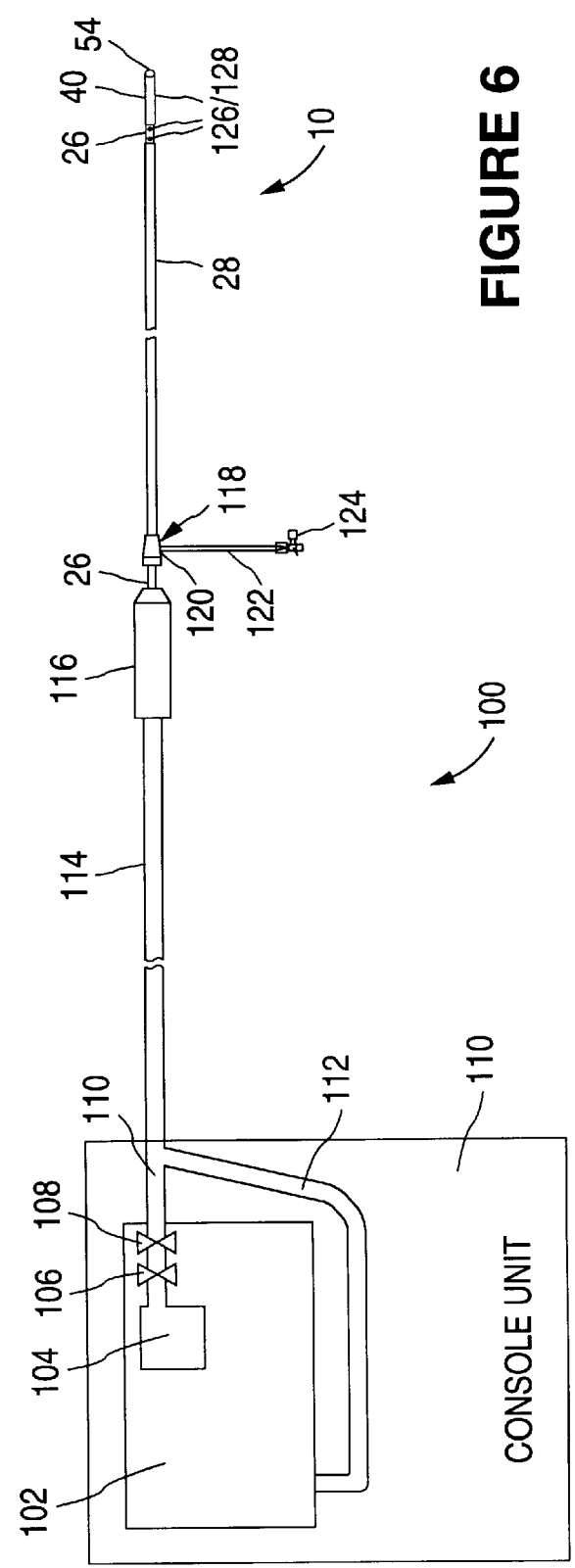
FIG. 6 is a longitudinal, side-elevational view of a system for cooling biological tissue which includes a source of a medium for cooling the tissue and a device, such as that shown in any of FIGS. 1 through 5, according to an embodiment of the present invention.

In a preferred embodiment, the first lumen 12, the expanding means 22, and the second lumen 14 form a closed media-flow pathway. That is, preferably, the first medium flowing in the first lumen flows into the expanding means to form the second medium flowing in the second lumen. The second medium then flows into a pressurizing means 104, as shown in FIG. 6 and further described in relation thereto, such as a compressor, to produce the first medium flowing in the first lumen. Thus, preferably, the media are continuously recycled during operation of the device. An example of a suitable closed media-flow pathway for use herein appears in the John D. Dobak, III, et al. Applications.

As shown in FIG. 1, a portion of the first lumen 12 and a portion of the second lumen 14 may be, and preferably are, housed in a catheter lumen 26. The catheter lumen 26 and the second lumen 14 may be in a fluid-tight relationship, for example, in a close, fixed relationship, as shown. The catheter lumen may be fixed relative to the second lumen by any variety of suitable means. For example, the catheter lumen may be fixed by way of adhesion to the second lumen.

As shown in FIG. 1, portions of the first lumen 12 and second lumen 14 are arranged substantially longitudinally within the catheter lumen 26. Preferably, the first and second lumens are so arranged to lie substantially parallel to one another and substantially coaxially about longitudinal axis L, as shown.

As further shown in FIG. 1, the expanding means 22 is of a diameter which is less than that of the second lumen, and preferably, less than that of the first and second lumens. Merely by way of example, the inside diameter of the expanding means 22 may be from about 0.005" to about 0.020", the inside diameter of the first lumen may be from about 0.015" to about 0.050", the inside diameter of the second lumen (based on the largest inside diameter in the bellows portion 40) may be from about 0.020" to about 0.150", and the outside diameter of the catheter lumen 26 may be from about 0.070" to about 0.170". These dimensions may vary depending on the particularities, such as size, shape and accessibility, of the tissue being treated. For example, the above-mentioned dimensions are particularly suitable when the device 10 is used in the treatment of cardiopulmonary tissue.

When the first medium, which is at a first temperature in the distal portion 20 of the first lumen, flows through the expanding means 22, into the larger, distal portion 36, or expansion chamber, of the second lumen, it expands to form the second medium, which, by virtue of the expansion, is at a lower temperature, relative to the first temperature, in the distal portion 36 of the second lumen. This lower temperature of the second medium is sufficient for cooling of the tissue and may be sufficient for adhering a contact portion of the device to the tissue, for mapping the tissue, or for forming a lesion in the tissue, as further described herein.

In a preferred embodiment of the invention, portions of the first and second lumens are in a heat-exchange relationship, generally indicated by reference numeral 32, whereby the cold second medium pre-cools the first medium. Any of a variety of known heat-exchange relationships and means may be used, such as an efficacious, cross-current, heat-exchange relationship, as shown. An example of a suitable heat-exchange relationship for use herein appears in the John D. Dobak, III, et al. Applications.

The term "lumen" is used herein to refer to a substantially longitudinal structure, having an open, or hollow, interior, which may be in any variety of shapes consistent with its usage as a media-flow conduit, usage as a housing for another lumen, or other usage. That is, the lumens shown in the drawings have been illustrated as being substantially cylindrical, merely by way of convenience, not by way of limitation. Thus, any lumen diameter described herein is contemplated as being an effective lumen diameter, accounting for the shape, configuration, or other relevant particulars of the lumen, unless otherwise indicated or understood. Preferably, the lumens are substantially cylindrical, as shown.

The first lumen 12 may be composed of a variety of materials, such as plastics and/or elastomers, braided or unbraided; super-elastic metal alloys, such as super-elastic nickel titanium alloys, for example, nitinol; metals, such as stainless steel, platinum and titanium; and any combination thereof. Preferably, the material is a biocompatible material, such as polyimide.

The catheter lumen 26 may be composed of a variety of materials. Generally, it is composed of a biocompatible material, such as biocompatible polymer, polyimide, polyurethane, elastomeric plastic, and any combination thereof. Preferably, the material has good flexibility and strength, stability at low temperatures, compatibility with refrigerant (such as Freon), and manufacturability into a very thin lumen. Preferably, the catheter lumen is composed of a biocompatible polymer, such as polyether block amide which is commercially available as Pebax from Elf Atochem of Philadelphia, Pa., with a polyimide liner. Preferably, the catheter lumen is an insulator, insulating unselected tissue from undesired cooling. By way of example, a catheter lumen composed of polyether block amide of a thickness of greater than or equal to about 0.01 inches provides appropriate insulation.

The second lumen 14 is of a construction sufficient for contact between a contact portion 34 of the second lumen and the tissue. This contact portion may lie anywhere along an exposed surface 34 of the second lumen. When a catheter lumen 26 is employed, the contact portion 34 may lie anywhere along a portion of the second lumen which is distal to the catheter lumen, as shown in FIG. 1. The second lumen is also of a construction sufficient, for example, of an appropriate effective lumen diameter, such that the second medium flows through the contact portion with a pressure drop sufficient to provide a high cooling capacity in the contact portion. By way of example, in at least the contact portion, the second lumen may be substantially (that is, excluding the distal end portion 54 which may have a variable diameter, as shown) of a singular diameter, for example, the largest inside diameter of bellows portion 40, as shown in FIGS. 1 and 2, such that the pressure drop is low or minimal.

Figure 8:
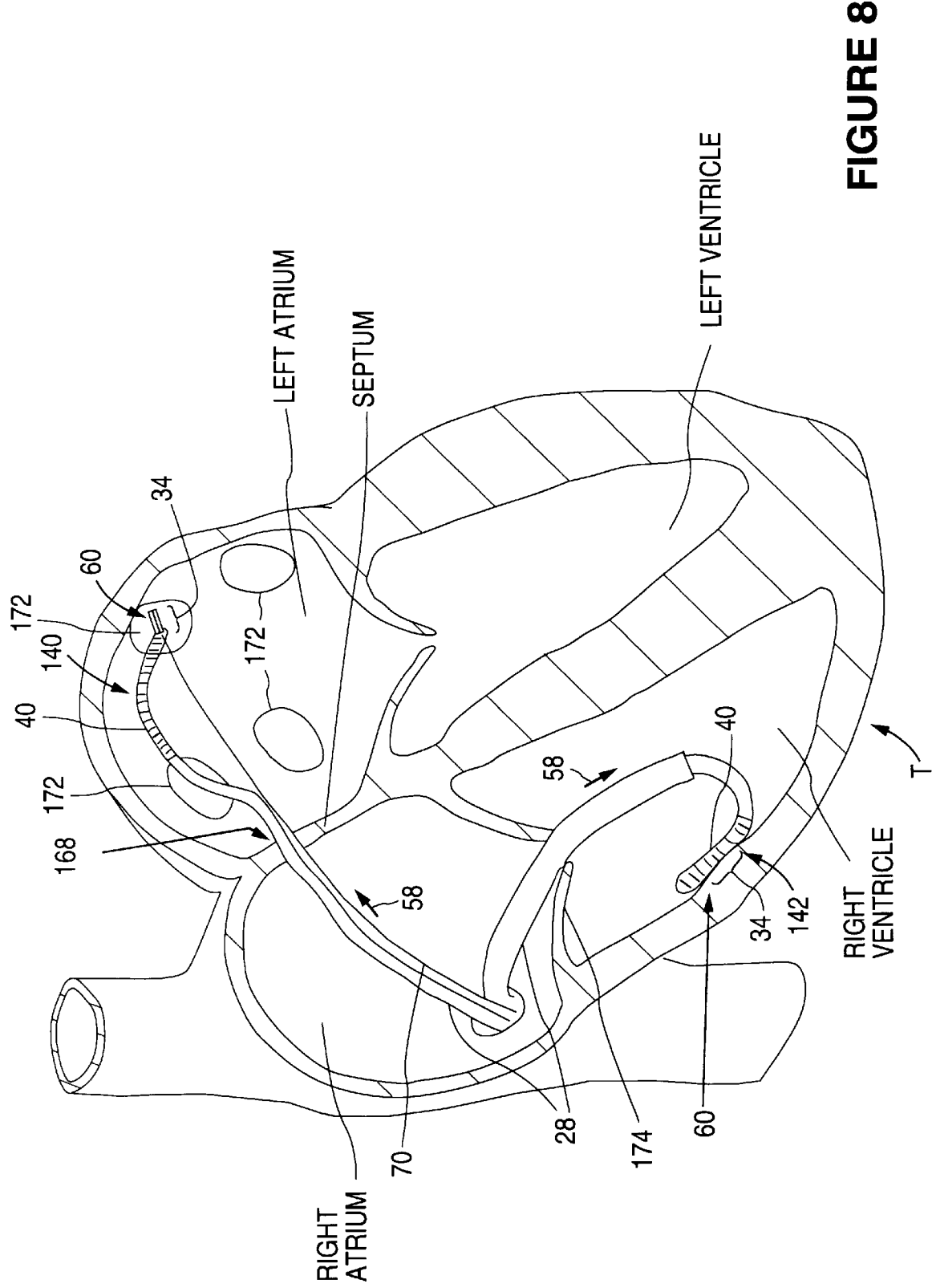
FIG. 8 is a schematic illustration of a device, such as that shown in any of FIGS. 1 through 5, placed in contact with biological tissue, according to an embodiment of the present invention.

Because the tissue to be contacted may be of an irregular or complex shape, or may be difficult to access, at least the contact portion 34 of the second lumen has a flexibility sufficient for tissue contact, such as the contact illustrated in FIG. 8. Thus, preferably, at least the contact portion is composed of a material of sufficient flexibility, over an operating temperature range, for contact between the contact portion and the tissue.

This operating temperature range is preferably from about a normal temperature of the tissue, for example, the tissue temperature existing at the time of placement of the contact portion in contact with the tissue before cooling of the tissue, for example, normal body temperature, to a temperature of the second medium at the contact portion which is sufficient for the desired cooling of the tissue, for example, that sufficient for forming a lesion in the tissue. This operating temperature range is generally from about normal body temperature to from about −20° C. to about −150° C., and preferably, from about normal body temperature to from about −70° C. to about −120° C.

Within this operating temperature range are cooling temperatures useful for adhering the contact portion to the tissue, namely, less than or equal to about 0° C., and for cold-mapping cardiopulmonary tissue, namely, at about −10° C. Thus, upon placement of the contact portion in contact with the tissue, the second medium may be cooled to adhere the contact portion to the tissue, for example, to anchor the contact portion to selected tissue, further cooled to cold-map the tissue, for example, to cold-map cardiopulmonary tissue, and yet further cooled to form a lesion in the tissue, as described above.

Materials of sufficient flexibility for the contact portion 34 of the second lumen include metal alloys, such as highly elastic, nickel-titanium alloys; pure metals, such as stainless steel, platinum and titanium; and elastomeric, biocompatible polymers, such as elastomeric plastics. A particularly preferred material is the super-elastic, nickel-titanium alloy, nitinol, a flexible material having a high fatigue lifetime.

In a preferred embodiment, the entire second lumen 14 is composed of one of these suitable materials, which is most preferably nitinol. Alternatively, portions of the second lumen other than the contact portion may be composed of a material which is not thermally conductive, for example, to protect certain portions of the tissue from undesired cooling or to minimize heat loss from the second medium where cooling is not desired. In this alternative embodiment, the material which is not thermally conductive is preferably of a flexibility sufficient to facilitate contact between the contact portion and the tissue.

In a particular embodiment of the invention, the contact portion 34 is of a construction sufficient for contact with a elongated portion 60 of the tissue, as shown in FIG. 8. This embodiment is preferred for many applications in which cooling of an elongated portion of tissue is desired, such as the treatment of atrial fibrillation.

FIG. 1 shows one such preferred embodiment, in which the expanding means is located at a longitudinal position 46. The second lumen 14 includes a first portion 50 which is distal relative to position 46 and a second portion 52 which is proximal to position 46, both portions being distal of the catheter lumen 26. In the first portion 50, the second medium initially flows in a distal direction in the second lumen, while in the second portion 52, the second medium generally flows in a proximal direction in the second lumen, as shown by the directional arrows 18. In this embodiment, the second medium is coldest in the distal portion 36 of the second lumen nearest the expanding means 22, that is, adjacent longitudinal position 46. The first and second portions of the second lumen are of a construction sufficient for contact between the contact portion 34 and the selected portion 60 of the tissue, as shown, for example, in FIG. 8, to cool the tissue. Preferably, the contact portion 34 is of a length of from about 3 to about 15 centimeters for contact with an elongated portion of the tissue, although other suitable lengths may be used.

FIG. 2 shows another such preferred embodiment, in which the expanding means is located at a longitudinal position 48 which is proximal relative to the longitudinal position 46 shown in FIG. 1. The second lumen 14 includes a first portion 50 which is distal relative to position 48 and a second portion 52 which is proximal to position 48, both portions being distal of the catheter lumen 26. In this embodiment, the flow of the second medium is substantially as described above in relation to FIG. 1 (although there may be a slightly greater initial flow in the distal direction in the first portion, given the longer length between position 48 and the distal end portion 54 relative to that between position 46 and the distal end portion 54 shown in FIG. 1). That is, upon expansion through expanding means 22, the second medium tends to flow proximally to the low pressure second portion of the second lumen, rather than distally to the distal end of the second lumen. In this embodiment, the second medium is coldest in the distal portion 36 of the second lumen nearest the expanding means 22, that is, adjacent longitudinal position 48. The first and second portions of the second lumen are of a construction sufficient for contact between the contact portion 34 and the selected portion 60 of the tissue, as shown, for example, in FIG. 8, to cool the tissue. As described above, the contact portion 34 is preferably of a length of from about 3 to about 15 centimeters for contact with an elongated portion of the tissue, although other suitable lengths may be used.

In a particularly preferred embodiment, the first portion 50 includes a distal cap 54, which may be rounded as shown in FIGS. 1 and 2, although other shapes are contemplated, particularly those conforming to the shape of the tissue to be contacted. Whatever its shape or form, the distal cap is preferably smooth along any tissue-contacting portion thereof, for example, to facilitate maneuverability of the device and to avoid damage to the tissue. The distal cap may be an integral part of the second lumen, as shown in FIGS. 1 and 2, or an attachment to the second lumen, as shown in FIG. 5.

The configurations of the device 10 shown in FIGS. 1 and 2, may be static or, preferably, changeable. That is, the expanding means 22 may be fixed at, or selectively moved to, a longitudinal position 46 shown in FIG. 1, a longitudinal position 48 shown in FIG. 2, or other longitudinal position, to form a cooling region at a desired position along the length of the device 10. For example, when the expanding means is located at position 46, the second medium is at its lowest temperature adjacent thereto, such that the greatest cooling occurs at the distal portion 36 of the second lumen, including the distal cap 54, and a distal section of the bellows portion 40 adjacent position 46, as shown in FIG. 1. When the expanding means is located at position 48, the second medium is at its lowest temperature adjacent thereto, such that the greatest cooling occurs at distal portion 36 of the second lumen and a section of the bellows portion 40 adjacent position 48, as shown in FIG. 2.

Thus, according to the present invention, one can select a position along a length of the device 10 where the greatest cooling is desired, which preferably lies adjacent the contact portion 34 of the device, either by choosing such a device with the expanding means fixed at the desired position, or adjusting such a device such that the expanding means is at the desired position. When the contact portion is placed against the tissue, cooling of the tissue adjacent the contact portion, such as the elongated portion 60 of tissue shown in FIG. 8, may be obtained.

The bellows portion 40 of the device 10 may be longitudinally fixed to have a particular length, such as that shown in FIGS. 1 and 2. By way of example, conventional guiding means (not shown), such as internal or external guide wires, may be used to maintain a fixed longitudinal position of the bellows portion. Alternatively, the bellows portion may be longitudinally moveable, for example, in an accordion-type manner, such that its length may be expanded or contracted (not shown). In the latter case, the shape and dimension of the bellows portion is adjustable, for example, to correspond to the shape and dimension of the tissue. The longitudinal movement may be achieved by manipulating the second lumen 14 relative to the tissue, such as by adhering the second lumen to the tissue and then pulling the second lumen away from the tissue for extension, or by pushing the second lumen against the tissue for contraction. The catheter lumen 26 may be used to facilitate any such manipulation. Conventional guiding means, such as internal or external guide wires, may also be used to facilitate any such manipulation. Examples of guiding means and the uses thereof are further described herein, particularly in relation to FIGS. 3 through 5.

According to alternate embodiments of the present invention, a sheath lumen 28 of the device 10 may be used to control the location or length of the contact portion 34 along the length of the device, as further described in relation to FIGS. 3 and 4. That is, the sheath is larger in diameter than the second lumen 14 and/or the catheter lumen 26 shown in FIGS. 1 and 2, such that it houses at least a portion of the second lumen and/or catheter lumen and may house at least a portion of the bellows portion 40 of the device. Thus, the outside diameter of the sheath 28 is larger than that of the second lumen and/or the catheter lumen previously described. This diameter is generally from about 0.100" to about 0.200", and preferably from about 0.104" to about 0.156".

In these alternate embodiments, the sheath may fixed at, or selectively positionable at, a longitudinal position along the length of the device, to cover a portion of thereof, such that cooling in the covered portion is either reduced or substantially eliminated. The contact portion 34, where cooling takes place, is thus fixed or selectable, in longitudinal position and/or length. This allows the user additional control as to the tissue site and/or length of the tissue adjacent the contact portion which is to be cooled, as shown in FIG. 8.

In the fixed embodiment, the sheath may be fixed relative to the second lumen by any variety of suitable means, in the desired longitudinal position. For example, the sheath may be fixed by way of a close or friction fit between it and the second lumen, or by way of adhesion to the second lumen. Further by way of example, the sheath may house a catheter lumen, such as that described in relation to FIGS. 1 and 2, and be fixed by way of a close or friction fit between it and the catheter lumen, or by way of adhesion to the catheter lumen.

In the changeable embodiment, the sheath is moveable in a longitudinal direction, such as the distal and proximal directions represented by bidirectional arrow 60 shown in FIGS. 3 and 4, to obtain the desired longitudinal positioning. By way of example, the sheath may be distanced from the second lumen by a gap 56 to provide a substantially free or frictionless movement of the sheath relative to the second lumen. Alternatively, an inner surface of the sheath and an outer surface of the second lumen may be designed for a sliding engagement therebetween, such that the sheath is slidably moveable relative to the second lumen. In a similar manner, if the sheath houses a catheter lumen (not shown), as described above, the sheath may be distanced from the catheter lumen or designed for slidable engagement with the catheter. Just as the sheath may be longitudinally moveable with respect to the second and/or catheter lumen, the second and/or catheter lumen be longitudinally moveable within the sheath.

The sheath lumen 28 may be composed of a variety of materials, such as polymeric material. Preferably, it is composed of a biocompatible material, such as polyolefin. Preferably, the sheath lumen is an insulator, insulating unselected tissue from undesired cooling.

In a tissue treatment application, the contact portion 34 is placed in contact with the tissue to be treated, such as an elongated portion 60 of the tissue T, as shown in FIG. 8. This may involve maneuvering, such as twisting, pushing or pulling on, the sheath 28, the catheter lumen 26, or the second lumen 14. For example, as schematically shown in FIG. 8, the sheath 28 may be pushed in a distal direction represented by directional arrow 58. As described above, the contact portion 34 of the second lumen may be of predetermined longitudinal position and/or length appropriate for contact with the tissue. Alternatively, the placement of the contact portion 34 may involve selecting a longitudinal position and/or length thereof appropriate for contact with the tissue, as described above. Further, the placement of the contact portion 34 may involve guiding the contact portion to the tissue to be treated, as further described in relation to FIGS. 3 through 5.

Appropriate placement of the device may be facilitated by use of a catheter lumen 26 of a predetermined shape, strength and/or flexibility, without recourse to additional guiding means. Placement may also be facilitated by manipulating the bellows portion 40 to take on various shapes or orientations, for example, bending the bellows portion such that it is shaped or orientated appropriately for the desired contact. Appropriate placement of the device may also be facilitated by use of a sheath lumen 28 of a predetermined shape, strength and/or flexibility, without recourse to additional guiding means. Alternatively, guiding means 70 may be employed in various modes and manners, such as those shown in FIGS. 3 through 5.

FIG. 3 shows a guiding means 70, which may be in the form of a guide wire 70, at least partially housed within sheath 28 and longitudinally disposed along a length of the device 10. The guide wire may be static or longitudinally moveable relative to the device. As shown in FIG. 3, the guide wire may contact the outside of the second lumen 14. FIG. 4 shows a guiding means 70, at least partially housed within sheath 28 and longitudinally disposed along a length of the device 10, wherein the distal end of the device is attached to the guiding means via attachment means 72. By way of example, attachment means 72 may be a housing having a lumen therein for receiving a guide wire 70, as shown. As shown in FIG. 4, the guide wire may be distanced from the outside of the second lumen 14. The device may be fixed relative to the guide wire or longitudinally moveable relative to the guide wire, as represented by bidirectional arrow 74. FIG. 5 shows internal guiding means 70, which is fixed to the second lumen and may be longitudinally fixed or longitudinally moveable within the device 10 by any appropriate means. Whether fixed or moveable, the guiding means is preferably of sufficient flexibility and/or lumen-support characteristics to facilitate contact between the contact portion of the device and the tissue. By way of example, the guiding means may be composed of a flexible and/or lumen-supportive material, such as stainless steel or any known material.

According to the embodiments shown in FIGS. 3 and 4, typically, the guiding means is placed in relation to the tissue to be treated, whereupon the sheath 28 is moved along the guiding means to bring the contact portion 34 of the second lumen 14 into contact with the tissue. According to the embodiment shown in FIG. 5, typically, the internal guiding means is used to support the second lumen during its placement in relation to the tissue. In any of these embodiments, the guiding means may be retracted upon appropriate placement of the second lumen. Generally, the guiding means may be configured and employed as described above or in other ways known in the art.

As shown in FIGS. 1 and 2, device 10 may include, and preferably does include, means 62 for sensing a temperature of the tissue or a temperature of the media flowing through the device. By way of example, such means may be a thermistor, a thermocouple, a thermometric semiconductor device, the like, and any combination thereof. Temperature-sensing means 62 may be located wherever temperature readings are desired, such as in, along or adjacent the first lumen 12, particularly the distal portion 20 thereof, the expanding means 22, and the second lumen 14, particularly the proximal portion 36 and/or the contact portion 34 thereof. Such means 62 may also be located in the heat-exchange area 32 of the device. Such means may be placed inside a lumen, for example, when a temperature reading of media therein is desired, outside a lumen, for example, when a temperature reading of tissue is desired, or otherwise suitable to the temperature reading desired. Temperature-sensing means 62 may be wired through the device in any known way.

A system 100 for cooling biological tissue which includes device 10 and a source 102 of the first medium therefor, is shown in FIG. 6. The device 10 shown in FIG. 6 includes the first lumen 12 (not shown), the expanding means 22 (not shown), and second lumen 14 (partially shown), as described above, disposed within an optional sheath 28, as also described above, wherein the second lumen includes bellows portion 40 and distal cap 54.

The source 102 of first medium may include means 104 for pressurizing the first medium, such as a compressor, and preferably, an oil-free compressor to reduce contamination of the first medium. The compressor may be controlled by means for controlling the compression rate, for example, electrical means (not shown), such as means for controlling the electrical current to adjust the speed of the compressor motor, or mechanical means (not shown), such as valve means for controlling the flow of the first medium therethrough, or other known means.

The source 102 is operably connected to a proximal portion 110 of the first lumen 12 for flow of the first medium therein. Means 106 for controlling the pressure of the first medium and/or means 108 for controlling flow of the first medium, such as pressure valves and/or flow valves, respectively, may be disposed along the proximal portion 110, as shown, and employed as known. In a similar manner, means (not shown) for controlling the pressure of the second medium and/or means (not shown) for controlling flow of the second medium, such as pressure valves and/or flow valves, respectively, may be disposed along the proximal portion 112 of the second lumen and employed as known.

In a preferred embodiment, the source 102 is also operably connected to a proximal portion 112 of the second lumen 14 for receiving the second medium upon its return from the proximal end of the device 10, so that the second medium is recycled within the system, as described above, as opposed to being, less preferably, exhausted from the system. That is, in a preferred embodiment, the second medium flows into source 102 wherein it is pressurized, for example, via pressurizing means 104, to become the first medium flowing into the proximal end 110 of the first lumen.

The source 102, pressurizing means 104, and controlling means 106 and/or 108, and the like, may be housed in a console unit 110, for convenience, as shown. In FIG. 6, the first and second lumens which are operably connected to the source 102, are generally represented by media channel 114 between the console unit 110 and the handle 116, merely by way of convenience, not by way of limitation. As generally shown, the source 102 may be, and preferably is, operably connected to a handle 116 via this media channel.

Preferably, the handle 116 includes means for controlling the cooling operation. That is, the handle preferably carries controls for system 100, such as a control for turning the system on and off, a control for providing media flow from the source, a control for selecting a pressure and/or flow of the first medium and/or second medium, the like, and any combination thereof. Other possible features of the handle 116 are described herein in relation to FIG. 7.

The second lumen 14 (with first lumen 12 lying therein) exits the handle 116, optionally within catheter lumen 26, as shown in FIG. 6. The catheter lumen may be connected to a means 118, such as a junction, for providing or controlling communication with the sheath 28 and other fluids. By way of example, means 118 may include a hemostasis valve 120 to reduce or to prevent the flow of blood from the body, as is known. Further by way of example, means 118 may include a channel 122 for flushing fluid, such as blood, from the system 100 in a distal direction. In the latter case, a flushing fluid, such as a biologically compatible saline fluid, may be provided via channel 122 and controlled via a flow-control valve 124. The flushing fluid travels to means 118 to be flushed distally along sheath 28, such as, and preferably, through the gap 56 between the second lumen and the sheath 28, as shown in FIGS. 3 and 4. The flushing fluid thus flushes blood from the device 10 and/or from the treatment site.

In FIG. 6, the device 10 is shown as including stimulating means 126 and/or sensing means 128 proximal of the portion 40 of the second lumen. Means 126 may be means for stimulating electrical activity of the tissue or "pacing", for example, when the tissue to be treated is cardiopulmonary tissue (as further described herein), and means 128 may be means for sensing electrical activity of such tissue.

Means 126 and 128 may be used for electrophysiological mapping of the tissue, by known procedures. For example, these means may be used for electrophysiological mapping of cardiopulmonary tissue to determine a site of a disturbance in the electrical activity or rhythm of the tissue, where treatment is desired. Means 126 and 128 may also be used in a cold-mapping of cardiopulmonary tissue, such as by the "ice-mapping" procedure disclosed in the above-referenced Milder patent, which is incorporated herein by this reference, as further described herein.

Generally, means 126 and means 128 are electrode devices, although any appropriate stimulating means and/or sensing means may be used. Electrically active bands, rings or partial rings, strips, and the like (not shown) may also be disposed along bellows portion 40 of the second lumen to facilitate electrophysiological study, as generally shown by means 126/128 located on bellows portion 40 in FIG. 6. Means 126, means 128, and any electrical means 126/128 employed along bellows portion 40, may be wired through the device by any known means.

Figure 7:
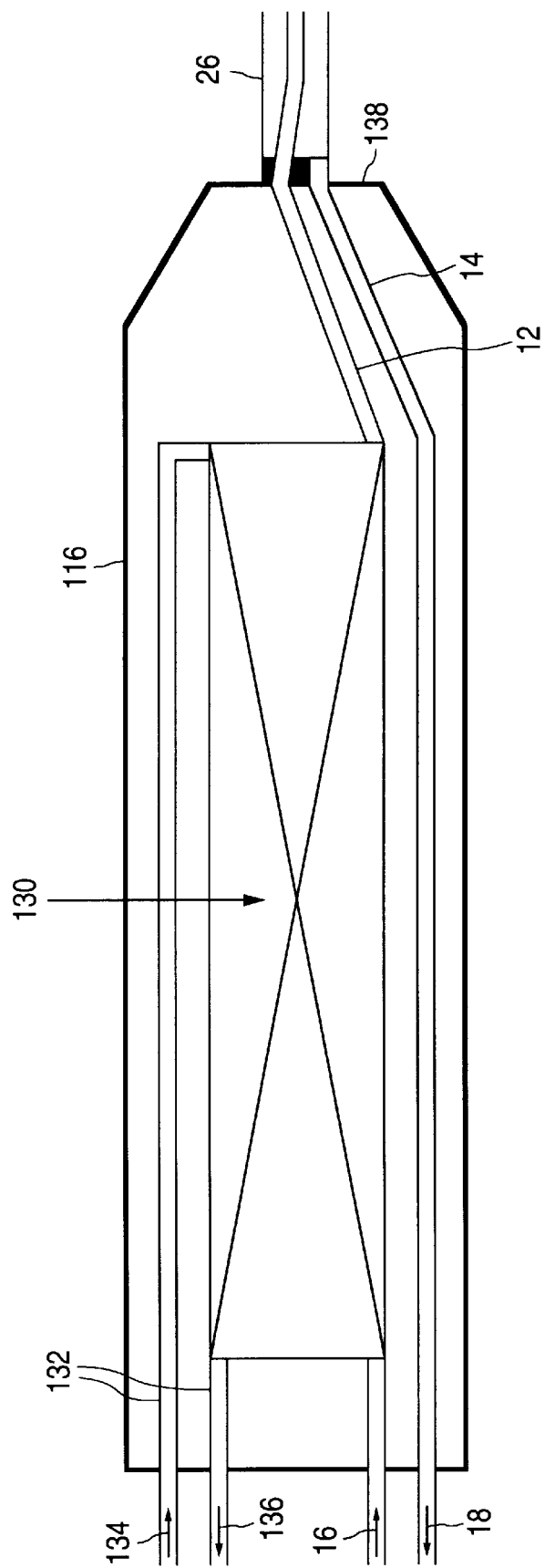
FIG. 7 is a side-elevational view of a portion of the system shown in FIG. 6, said portion including means for heat exchange between at least two lumens, said portion shown enlarged and in longitudinal cross-section, according to an embodiment of the present invention.

A particularly preferred embodiment is now described in relation to FIG. 7, which generally shows an enlarged view of the handle 116 described above. The first lumen 12 and the second lumen 14 are shown longitudinally disposed in the handle, with the first medium and the second medium, respectively, flowing therethrough, as represented by arrows 16 and 18. In this embodiment, the first lumen 12 and a third lumen 132, having a third medium flowing therethrough, also shown longitudinally disposed in the handle, are in a heat-exchange relationship, as generally represented by reference numeral 130. Any appropriate heat-exchange means, and flow pattern, may be used. Preferably, the third medium flows through the third lumen, into the handle, as represented by directional arrow 134, and out of the handle, as represented by directional arrow 136, for counter-current heat-exchange, although a reverse flow pattern or other efficacious flow pattern is also possible.

The third lumen may take, and preferably does take, the form of a closed flow pathway for the third medium, such that the third medium is recycled, as opposed to being, less preferably, exhausted from the system. This closed flow pathway includes a source (not shown) of the third medium which is operably connected to the third lumen. This closed flow pathway may also include a means for pressurizing the third medium (not shown), operably connected to the source, such as a compressor. The source and compressor may be similar to those previously described in relation to the first medium. Merely by way of example, the source of the third medium and the compressor may be located in the console unit 110 of FIG. 6 and the third lumen may lie within media channel 114 of FIG. 6. The third lumen may also include an expanding means (not shown) for cooling the third medium, as previously described in terms of the expansion of the first medium to form the cooler second medium. An example of a suitable closed media-flow pathway for use herein appears in the John D. Dobak, III, et al. Applications.

Preferably, the handle 116 includes means for controlling the pre-cooling operation. That is, the handle preferably carries pre-cooling controls (not shown) for system loo, such as a control for providing flow of the third medium from its source, a control for selecting a pressure and/or flow of the third medium, the like, and any combination thereof. These pre-cooling controls may be similar to the controls previously described in relation to the first or the second medium.

The third medium flowing within the third lumen is of a temperature sufficient to pre-cool the first medium at a location proximal to the distal end 138 of the handle. Generally, this temperature is from about 0° C. to about −80° C., and preferably, from about −45° C. to about −80° C., when provided to the handle 116. When the first medium is pre-cooled in this manner, the device 10 provides maximal cooling upon expansion through the expanding means 22. An example of a suitable dual closed-loop system (i.e., including a closed pre-cooling loop and a closed cooling loop) for use herein is that described in the John D. Dobak, III, et al. Applications.

Whether the first medium is pre-cooled or not, it must be sufficient for the cooling desired. By way of example, the first medium may be, and preferably is, selected from the refrigerant mixtures R-23, R-503, R-13 and R-508B, which are commercially available from DuPont Fluoroproducts of Wilmington, Del., and any combination thereof. Preferably, the first medium is R508B, which is a mixture of trifluoromethane and haxafluoroethane. Most preferably, the mixture of trifluoromethane and hexafluoroethane comprises 30 weight percent to 50 weight percent trifluoromethane, for example, such a mixture commercially available under the identifier SUVA-95 from DuPont Fluoroproducts of Wilmington, Del.

When the first medium is pre-cooled, the third medium may be any appropriate medium for pre-cooling the first medium to the desired temperature. For example, the third medium may be, and preferably is, selected from halogenated hydrocarbon refrigerant mixtures, such as R-507, which is a mixture of 1,1,1-trifluoroethane and pentafluoroethane, and R-410A, which is a mixture of difluoromethane and pentafluoroethane, and any combination thereof. Preferably, the mixture of 1,1,1-trifluoroethane and pentafluoroethane comprises 50 weight percent of each component, for example, such a mixture commercially available under the identifier AZ-50 from Allied Signal Chemicals of Morriston, N.J. Preferably, the mixture of difluoromethane and pentafluoroethane comprises 50 weight percent of each component, for example, such a mixture commercially available under the identifier AZ-20 from Allied Signal Chemicals of Morriston, N.J.

As described above, the device 10 preferably has a second lumen 14 which includes a bellows portion 40. Alternatively, and less preferably, the device has a second lumen 14/26, which includes a lumen portion 200 of an approximately uniform diameter, as shown in FIGS. 9 and 10. That is, the walls of lumen portion 200 are approximately straight in longitudinal cross-section.

According to this embodiment, the second lumen 14/26 may be essentially the same as the second lumen 14, previously described in relation to FIGS. 1 through 5, with the exception of the bellows portion 40. In this case, a sheath lumen 26 (not shown) may be used in the manner previously described in relation to FIGS. 3 and 4. Alternatively, the second lumen 14/26 may be an extension of the catheter lumen 26, previously described in relation to FIGS. 1 through 5, up to a distal end 202. In the latter case, the second lumen 14/26 may be capped with distal end cap 204, as shown. Such a distal end cap 204 must be in a fluid-tight relationship with the distal end 202. This fluid-tight relationship may be established by any known means, for example, by use of a fluid-tight seal or by use of cover (not shown) placed over the distal end cap and extending proximally therefrom over at least a portion of second lumen 14/26 in a sealed relation thereto.

According to this alternative embodiment, the lumen portion 200 is of a predetermined length, while the expansion means 22 is longitudinally moveable therein so that the cooling or contact portion 34 can be moved to a desirable longitudinal position along the lumen portion for optimal cooling of the selected tissue. That is, the expansion means may be moved to the longitudinal position 206 of FIG. 9, the longitudinal position 208 of FIG. 10, or another longitudinal position. Desirable longitudinal positioning is that previously described in relation to FIGS. 1 and 2. When a sheath 26 is used, as described above, it may be longitudinally moveable relative to the second lumen 14/26 to cover at least a portion of lumen portion 200, and thereby adjust the length of the contact portion 34, as previously described in relation to FIGS. 3 and 4.

While the lumen portion 200 may be of any material previously described in relation to the contact portion 34, the bellows portion 40, the second lumen 14, or the catheter lumen 26, preferably, the lumen portion is of the same material as that previously described in relation to catheter lumen 26. Most preferably, the lumen portion 200 is composed of a biocompatible polymer, such as polyether block amide which is commercially available as Pebax for Elf Atochem of Philadelphia, Pa. Preferably, the polyether block amide is less than or equal to about 0.13 inches thick, for sufficient thermal conductivity. As in the preferred embodiment, the second lumen 14/26 is of a construction sufficient for contact between a contact portion 34 thereof, adjacent the expansion means 22, and a selected portion of the tissue.

The device 10 of this alternative embodiment may include any practicable combination of features described herein, for example, the temperature-sensing features shown in FIGS. 1 and 2, and the guiding features shown in FIGS. 3 through 5, and may be used in place of the device 10 in the system 100 of FIGS. 6 and 7. The device 10 and system 100 according to this embodiment may be used to cool biological tissue, as described herein, including the cardiopulmonary tissue described in relation to FIG. 8.

That is, according to the present invention, the device 10 and system 100 may be used to cool a wide variety of biological tissue, such as tissue within a body, preferably using minimally invasive procedures, such as percutaneous, intraarterial or intravenous procedures. The tissue may be tissue of an organ. This tissue may be tissue affected with an undesirable condition, benign or malignant, such as a growth or a tumorous or cancerous condition. While not so limited, the device 10 and system 100 are particularly suited for the cooling of cardiopulmonary tissue, as now described in relation to FIG. 8.

FIG. 8 shows the anatomy of cardiopulmonary tissue which is advantageously treated according to the present invention. Generally, many of the anatomical structures of cardiopulmonary tissue have proved to be difficult to access through the various passageways of the tissue, and/or difficult to contact for effective treatment by virtue of their location or shape, using prior art devices.

FIG. 8 shows various anatomical structures of the cardiopulmonary tissue, including the right atrium, the left atrium, the septum, the right ventricle, and the left ventricle. In the septum lies the fossa, represented by an opening 168, a structure which is often unformed in infancy, such that septum is open to transeptal passage of the device therethrough, and usually formed beyond infancy, such that the septum is closed and must be opened, by known means, for transeptal passage therethrough. In the left atrium lies pulmonary veins, as represented by openings 172.

As shown in FIG. 8, the device of the present invention, shown in various sizes and positions, as represented by configurations 140 and 142, is well-suited to accessing and to treating such structures. That is, the device 10 may be channeled to the heart using known percutaneous, intraarterial methods, arriving at the right atrium, for example, as shown in FIG. 8.

Appropriate positioning of the device may be facilitated by use of a sheath 28 of a predetermined shape or flexibility. Merely by way of example, the sheath may bent or angled or of a flexibility suitable for a certain degree of bending, as particularly shown by configuration 142. Appropriate positioning of the device is also facilitated by appropriate maneuvering of the device, such as by pushing the device distally and by pulling the device proximally until it reaches the desired position, as shown by configurations 140 and 142. For example, the device may be so manipulated to bend the second lumen for appropriate placement of the contact portion of the device, as shown by configuration 142. A transeptal approach may be desired for appropriate positioning, as shown in configuration 140, in which case the septum is simply entered (if open, as often in infancy), or opened (if closed, as usual beyond infancy) and entered, by known procedures.

As shown by the configuration 140, the device may be placed in relation to atrial tissue and/or pulmonary tissue, such as any pulmonary vein 172. As further shown by the configuration 142, the device may be placed in relation to ventricular tissue. Such placements may be facilitated by a guiding means 70 (schematically shown), as previously described.

Generally, when the device 10 or system 100 is used to treat cardiopulmonary tissue, means 70 for guiding the device, such as at least one guide wire of sufficient flexibility, is channeled to the tissue. By way of example, a guide wire 70 may be channeled to the right atrium, through the septum (conveniently via the unformed or formed fossa 168), and into a pulmonary vein 172, to place the device as shown by configuration 140 in FIG. 8. Further by way of example, a guide wire 70 may be channeled to the right atrium, through valve 174, and into the right ventricle, to place the device as shown by configuration 142 in FIG. 8. Guide means may be channeled through the cardiopulmonary tissue along pathways other than the exemplary pathways shown in FIG. 8. Guide means may be so channeled directly or indirectly, such as via a catheter (not shown) or other means, as known. In this manner, guide means 70 is placed in the vicinity of the tissue to be treated.

Once guide means 70 is so placed, the device 10 is also placed in the vicinity of the tissue to be treated via the guide means. For example, the guide means may be threaded through sheath 28, as shown in FIGS. 3 and 4. The sheath 28 is then moved along the guide means to reach the tissue of interest, whereupon, if not already appropriately positioned, sheath 28, second lumen 14, and/or expanding means 22 may be longitudinally positioned, as described above, to adjust a position of, and/or a length of, the contact portion 34 of the second lumen appropriately for the desired contact with the tissue to be treated. Further, the bellows portion 40 may be adjusted in dimension or shape, as described above, for appropriate contact.

Alternative embodiments for guiding the device 10 to the tissue to be treated are possible, such as any means generally used for electrophysiological mapping of tissue and the like. For example, guide means may be sheath 28 of a predetermined shape or of sufficient steerability for appropriate placement of the device. Alternatively, guide means as shown in FIGS. 3 through 5, may be employed.

The device 10 or system 100 is useful for the treatment of cardiac tissue, for example, to address the conditions of tachycardia, such as atrial fibrillation. The device may also be used for the treatment of pulmonary tissue, for example, to form a lesion in a pulmonary vein for connection with a lesion in the cardiac tissue.

In such applications, the device may be used for electrophysiological mapping of the cardiopulmonary tissue, via stimulating means 126 and sensing means 128 described above, to locate a site of a disturbance in the electrical activity or rhythm of the tissue, and thus, an appropriate placement of the device relative to the tissue to be treated. The device 10 may then be placed relative to the tissue, such that the contact portion 34 is in contact with the tissue to be treated, as previously described. This placement may involve appropriate cooling of the contact portion to adhere the contact portion 34 to the tissue, as previously described, for example, to anchor the device for greater stability during treatment.

Once placed, the device may be used for cold-mapping of the tissue, whereby the contact portion 34 of the device is cooled, in the manner previously described, to a temperature sufficient to cause a temperature of the contacted tissue to be such that electrical activity therein is suppressed. This cold-mapping of the tissue, may substantially follow the "ice-mapping" procedure disclosed in the above-referenced Milder patent. Generally, for cold-mapping, the temperature of the contact portion of the device may be about $-10°$ C., such that the temperature of the contacted tissue may be about $5°$ C. for suppression of its electrical activity. According to one embodiment, the device may then be used to attempt stimulation of the tissue via stimulating means 126. If the disturbance in the electrical activity or rhythm of the tissue cannot be stimulated, as determined using sensing means 128, the contacted tissue is believed to be an appropriate site for the formation of a lesion therein. According to an alternate embodiment, after the cooling to suppress the electrical activity of the tissue, as described above, the device may then be used simply to sense any electrical activity of the tissue (that is, without the above-described stimulation of the tissue) to determine whether the contacted tissue is an appropriate site for formation of a lesion.

The device may be used for formation of such a lesion, whereby the contact portion 34 of the device is cooled, in the manner previously described, first to a temperature sufficient to cause the tissue to adhere to the contact portion, for example, to anchor the device 10, and then, to a temperature sufficient to cause a temperature of the contacted tissue to be such that a lesion is formed therein. While the first cooling (for adherence) is preferred, it is optional or may simply occur as the temperature is lowered to the lesion-forming temperature. The degree of cooling may be controlled by adjusting the pressure and/or flow of the cooling media, as previously described. Further, the degree of cooling may be sensed, measured and/or monitored using the temperature sensing means, as previously described.

For efficacious treatment of the tissue, the lesion formed is of sufficient length, continuity and/or depth to interrupt or to block electrical conduction across the lesion. Formation of the lesion may be monitored and controlled using ultrasonic imaging of the growing lesion during the treatment, by known procedures.

Using the device and system of the present invention, deep focal lesions, as well as deep, elongated and/or continuous lesions may be obtained. In the treatment of atrial fibrillation, the lesions should be sufficiently deep, elongated and/or continuous to make a complete conduction block across anatomical structures of the heart. The dimensions of such lesions will depend on the dimensions of the heart tissue being tissue, which typically vary quite a bit from patient to patient, for example, by virtue of patient size or degree of dilation of the heart tissue.

The device and system of the present invention, and methods of using same, provide advantageous means for accessing cardiopulmonary tissue, determining an appropriate site for forming a lesion therein, manipulating the device for appropriate tissue contact, and cooling the tissue to form an efficacious lesion therein.

While the present invention has been particularly described in relation to the treatment of cardiopulmonary tissue, for which the device and system are most usefully applied, the device and system of the present invention, and the methods of using same, also provide advantageous means for accessing other biological tissue, particularly tissue within the body, manipulating the device for appropriate tissue contact with a desired lesion site, and cooling the tissue to form an efficacious lesion therein.

Many of the advantages of the device and system of the present, and methods of using same, are also provided by a device and system, and methods of using same, that are disclosed in U.S. patent application Ser. No. 09/089,442, of John D. Dobak, III, entitled "CRYOGENIC DEVICE, SYSTEM AND METHOD OF USING SAME", filed concurrently with this application, which is incorporated herein by this reference.

Although the various aspects of the present invention have been described with respect to the preferred embodiments thereof, it will be understood that the invention is entitled to protection within the full scope of the appended claims.

It is claimed:

1. A cryogenic device for treating biological tissue, comprising:

at least two lumens, comprising: a first lumen for passage of a first medium, said first medium being pressurized and of a first temperature at a distal portion thereof; and a second lumen for passage of a second medium, said second lumen of a construction sufficient for contact between a contact portion thereof and a selected portion of the tissue, at least said contact portion of a material having a thermal conductivity sufficient for cooling of the tissue by said second medium flowing therethrough; and means for expanding said first medium to form said second medium, said expanding means disposed in a media-flow pathway between said first lumen and said second lumen, said expanding means longitudinally moveable within said second lumen;

wherein, upon expanding said first medium to form said second medium, said second medium is of a second temperature, said second temperature ranging from a temperature which is less than said first temperature to a temperature sufficient for cooling the tissue to form a lesion in the selected portion of tissue.

2. The device of claim 1, wherein said second temperature is at a minimum adjacent a longitudinal position of said expanding means.

3. The device of claim 2, wherein said contact portion is adjacent the longitudinal position of said expanding means.

4. The device of claim 1, wherein said second lumen includes a bellows portion.

5. The device of claim 4, wherein the bellows portion is composed of a material selected from a metal alloy and a metal.

6. The device of claim 1, wherein said second lumen includes a portion of approximately uniform diameter and of a predetermined length.

7. The device of claim 6, wherein the second lumen portion is composed of a biocompatible polymer.

8. A cryogenic method of treating biological tissue, comprising:
   providing at least two lumens, the at least two lumens comprising a first lumen for passage of a first medium, the first medium being pressurized and of a first temperature at a distal portion of the first lumen, and a second lumen for passage of a second medium, the second lumen including a bellows portion and a distal end of a construction sufficient for contact between a thermally conductive contact portion thereof and a selected portion of the tissue;
   providing means for expanding the first medium to form the second medium;
   longitudinally positioning the expanding means adjacent the contact portion;
   placing the contact portion in contact with the selected portion of the tissue; and
   expanding the first medium to form the second medium, whereupon the second medium is of a second temperature at the contact portion, the second temperature ranging from a temperature which is less than said first temperature to a temperature sufficient for cooling the tissue to form a lesion in the selected portion of the tissue.

9. A cryogenic device for treating biological tissue, comprising:
   at least two lumens, comprising: a first lumen for passage of a first medium, said first medium being pressurized and of a first temperature at a distal portion thereof, and a second lumen for passage of a second medium, said second lumen including a bellows portion and a distal end of a construction sufficient for contact between a contact portion thereof and a selected portion of the tissue; and
   means for expanding said first medium to form said second medium, wherein said expanding means is disposed in a media-flow pathway between said first lumen and said second lumen and a longitudinal position of said expanding means is selectable;
   wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue.

10. The device of claim 1 wherein a dimension of said bellows portion is selectable.

11. The device of claim 1, wherein a shape of said bellows portion is selectable.

12. The device of claim 1, wherein a dimension of said bellows portion is predetermined.

13. The device of claim 1, wherein a shape of said bellows portion is predetermined.

14. The device of claim 1, wherein at least the contact portion is composed of a material of sufficient flexibility over an operating temperature range for contact with the selected portion, said operating temperature range being from about a normal temperature of the tissue to said second temperature.

15. The device of claim 1, wherein at least the contact portion is composed of a material selected from a metal alloy and a metal.

16. The device of claim 15, wherein at least the contact portion is composed of a nickel-titanium alloy.

17. The device of claim 15, wherein at least the contact portion is composed of a metal selected from a group consisting of stainless steel, platinum, titanium, and any combination thereof.

18. The device of claim 1, further comprising means for guiding the contact portion to the selected portion.

19. The device of claim 18, wherein said guiding means comprises a guide wire operably connected to the distal end of said second lumen.

20. The device of claim 18, wherein said guiding means is a sheath which house at least a portion of said second lumen.

21. The device of claim 20, wherein said sheath is of a predetermined shape.

22. The device of claim 20, wherein said sheath is steerable.

23. The device of claim 20, further comprising at least one guide wire disposed within said sheath.

24. The device of claim 23, wherein said at least one guide wire is attached to the distal end of said second lumen.

25. The device of claim 20, further comprising at least one guide wire disposed within said second lumen.

26. The device of claim 25 wherein said at least one guide wire is attached to the distal end of said second lumen.

27. The device of claim 1, further comprising means for sensing a temperature of the tissue.

28. The device of claim 27, wherein said temperature-sensing means is disposed along a length of said bellows portion.

29. The device of claim 1, further comprising means for sensing a temperature of said first medium or said second medium.

30. The device of claim 29, wherein said temperature-sensing means is disposed adjacent said expanding means.

31. The device of claim 1, further comprising means for selecting a degree of cooling of the tissue.

32. The device of claim 31, wherein said selecting means includes means for selecting a pressure of said first medium or said second medium.

33. The device of claim 31, wherein said selecting means includes means for selecting a flow of said first medium or said second medium.

34. The device of claim 1, wherein said first lumen, said second lumen and said expanding means form a closed media-flow pathway.

35. The device of claim 1, wherein said expanding means allows for a media pressure drop thereacross.

36. The device of claim 1, wherein said expanding means is a means for restricting media flow.

37. The device of claim 1, wherein said expanding means is an orifice suitable for Joule-Thomson expansion.

38. The device of claim 1, wherein said at least two lumens further comprise a catheter lumen which houses at least a portion of said first and second lumens.

39. The device of claim 38, wherein said at least two lumens further comprise a sheath lumen which houses at least a portion of said catheter lumen.

40. The device of claim 39, wherein said sheath lumen is longitudinally moveable relative to any of said first, said second and said catheter lumens.

41. The device of claim 40, wherein a longitudinal position of said sheath lumen determines a dimension of the contact portion.

42. The device of claim 39, wherein any of said first, said second and said catheter lumens is longitudinally moveable relative to sheath lumen.

43. The device of claim 42, wherein a longitudinal position of said sheath lumen determines a dimension of the contact portion.

44. The device of claim 1, wherein at the distal portion of said first lumen, said first medium is at a pressure of from about 100 psig to about 400 psig.

45. The device of claim 44, wherein at the distal portion of said first lumen, said first medium is at a pressure of from about 150 psig to about 200 psig.

46. The device of claim 1, wherein said first temperature is from about 13° C. to about −80° C.

47. The device of claim 46, wherein said first temperature is from about −35° C. to −45° C.

48. The device of claim 1, wherein said second temperature is from about −20° C. to about −150° C.

49. The device of claim 1, wherein said second temperature is from about −70° C. to about −120° C.

50. The device of claim 1, wherein said first medium is selected from a group consisting of R-23, R-503, R-13, R-508B, and any combination thereof.

51. The device of claim 1, wherein the tissue is affected with an undesirable condition.

52. The device of claim 1, wherein the tissue is organ tissue.

53. The device of claim 1, wherein the tissue is cardiopulmonary tissue.

54. The device of claim 53, further comprising means for stimulating electrical activity of the tissue.

55. The device of claim 53, further comprising means for recording electrical activity of the tissue.

56. The device of claim 53, wherein said second temperature is sufficient for cold-mapping the tissue.

57. The device of claim 53, wherein said second temperature is sufficient for forming a lesion sufficient to interrupt electrical conduction across the lesion.

58. The device of claim 53, wherein said second temperature is from about −20° C. to about −150° C.

59. The device of claim 53, wherein said second temperature is from about −70° C. to about −120° C.

60. A cryogenic system for treating biological tissue, comprising the device of claim 1 and a source of said first medium operably connected to said first lumen.

61. The system of claim 60, wherein said first medium is selected from a group consisting of R-23, R-503, R-13, R-508B, and any combination thereof.

62. The system of claim 60, wherein said first lumen and said second lumen are in a heat-exchange relationship.

63. The system of claim 60, wherein said first lumen, said second lumen and said expanding means form a closed media-flow pathway.

64. The system of claim 60, wherein said at least two lumens comprises a third lumen for passage of a third medium sufficient for cooling of said first medium.

65. The system of claim 64, wherein said first medium is selected from a group consisting of R-23, R-503, R-13, R-508B, and any combination thereof.

66. The system of claim 64, wherein said third medium is at a temperature from about 0° C. to about −80° C.

67. The system of claim 64, wherein said third medium is at a temperature from about −45° C. to about −80° C.

68. The system of claim 64, wherein said first lumen and said third lumen are in a heat-exchange relationship.

69. The system of claim 64, wherein said third lumen forms a closed media-flow pathway.

70. The system of claim 64, wherein said third lumen includes an expanding means for cooling said third medium.

71. The system of claim 64, wherein said third medium is selected from a group consisting of halogenated hydrocarbon refrigerant mixtures, and any combination thereof.

72. A cryogenic device for treating biological tissue, comprising:

at least two lumens, comprising: a first lumen for passage of a first medium, said first medium being pressurized and of a first temperature at a distal portion thereof; and a second lumen for passage of a second medium, said second lumen including a bellows portion and a distal end of a construction sufficient for contact between a contact portion thereof and a selected portion of the tissue;

means for expanding said first medium to form said second medium, said expanding means disposed in a media-flow pathway between said first lumen and said second lumen; and means for guiding the contact portion to the selected portion, said guiding means including a sheath which houses at least a portion of said second lumen;

wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue.

73. The device of claim 72, wherein said sheath is of a predetermined shape.

74. The device of claim 72, wherein said sheath is steerable.

75. The device of claim 72, further comprising at least one guide wire disposed within said sheath.

76. The device of claim 75, wherein said at least one guide wire is attached to the distal end of said second lumen.

77. The device of claim 75, wherein comprising at least one guide wire disposed within said second lumen.

78. The device of claim 77, wherein said at least one guide wire is attached to the distal end of said second lumen.

79. A cryogenic device for treating biological tissue, comprising:

at least two lumens, comprising: a first lumen for passage of a first medium, said first medium being pressurized and of a first temperature at a distal portion thereof; a second lumen for passage of a second medium, said second lumen including a bellows portion and a distal end of a construction sufficient for contact between a contact portion thereof and a selected portion of the tissue; a catheter lumen which houses at least a portion of said first and second lumens; and a sheath lumen which houses at least a portion of said catheter lumen; and means for expanding said first medium to form said second medium, said expanding means disposed in a media-flow pathway between said first lumen and said second lumen;

wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue.

80. The device of claim 79, wherein said at least two lumens further comprise a sheath lumen which houses at least a portion of said catheter lumen.

81. The device of claim 80, wherein said sheath lumen is longitudinally moveable relative to any of said first, said second and said catheter lumens.

82. The device of claim 81, wherein a longitudinal position of said sheath lumen determines a dimension of the contact portion.

83. The device of claim 80, wherein any of said first, said second and said catheter lumens is longitudinally moveable relative to sheath lumen.

84. The device of claim 83, wherein a longitudinal position of said sheath lumen determines a dimension of the contact portion.

85. A cryogenic device for treating biological tissue, comprising:
at least two lumens, comprising: a first lumen for passage of a first medium, said first medium being pressurized and of a first temperature at a distal portion thereof, wherein said first temperature is from about 13° C. to about −80° C.; and a second lumen for passage of a second medium, said second lumen including a bellows portion and a distal end of a construction sufficient for contact between a contact portion thereof and a selected portion of the tissue; and
means for expanding said first medium to form said second medium, said expanding means disposed in a media-flow pathway between said first lumen and said second lumen;
wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue.

86. The device of claim 85, wherein said first temperature is from about −35° C. to −45° C.

87. A cryogenic device for treating biological tissue, comprising:
at least two lumens, comprising: a first lumen for passage of a first medium, said first medium being pressurized and of a first temperature at a distal portion thereof; and a second lumen for passage of a second medium, said second lumen including a bellows portion and a distal end of a construction sufficient for contact between a contact portion thereof and a selected portion of the tissue; and
means for expanding said first medium to form said second medium, said expanding means disposed in a media-flow pathway between said first lumen and said second lumen;
wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue and being from about −70° C. to −120° C.

88. A cryogenic device for treating cardiopulmonary tissue, comprising:
at least two lumens, comprising: a first lumen for passage of a first medium, said first medium being pressurized and of a first temperature at a distal portion thereof, and a second lumen for passage of a second medium, said second lumen including a bellows portion and a distal end of a construction sufficient for contact between a contact portion thereof and a selected portion of the tissue;
means for expanding said first medium to form said second medium, said expanding means disposed in a media-flow pathway between said first lumen and said second lumen; and
means for stimulating electrical activity of the tissue;
wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue.

89. The device of claim 88, further comprising means for recording electrical activity of the tissue.

90. The device of claim 88, wherein said second temperature is sufficient for cold-mapping the tissue.

91. The device of claim 88, herein said second temperature is sufficient fir forming a lesion sufficient to interrupt electrical conduction across the lesion.

92. The device of claim 88, wherein said second temperature is from about −20° C. to about −150° C.

93. The device of claim 88, wherein said second temperature is from about −70° C. to about −120° C.

94. A cryogenic system for treating biological tissue, comprising:
a cryogenic device for treating biological tissue, said cryogenic device comprising:
at least two lumens, comprising: a first lumen for passage of a first medium, said first medium being pressurized and of a first temperature at a distal portion thereof; a second lumen for passage of a second medium, said second lumen including a bellows portion and a distal end of a construction sufficient for contact between a contact portion thereof and a selected portion of the tissue; and a third lumen for passage of a third medium sufficient for cooling of said first medium;
and means for expanding said first medium to form said second medium said expanding means disposed in a media-flow pathway between said first lumen and said second lumen; wherein, upon expanding said first medium to form said second medium, said second medium is of a second temperature at said contact portion, said second temperature ranging from a temperature which is less than said first temperature to a temperature sufficient for cooling the tissue to form a lesion in the selected portion of tissue; and
a source of said first medium operably connected to said first lumen.

95. The system of claim 94, wherein said first medium is selected from a group consisting of R-23, R-503, R-13, R-508B, and any combination thereof.

96. The system of claim 94, wherein said third medium is at a temperature from about 0° C. to about −80° C.

97. The system of claim 94, wherein said third medium is at a temperature from about −45° C. to about −80° C.

98. The system of claim 94, wherein said first lumen and said third lumen are in a heat-exchange relationship.

99. The system of claim 94, wherein said third lumen forms a closed media-flow pathway.

100. The system of claim 94, wherein said third lumen includes an expanding means for cooling said third medium.

101. The system of claim 94, wherein said third medium is selected from a group consisting of halogenated hydrocarbon refrigerant mixtures, and any combination thereof.

102. A cryogenic method of treating biological tissue, comprising:
   providing at least two lumens, the at least two lumens comprising a first lumen for passage of a first medium, the first medium being pressurized and of a first temperature at a distal portion of the first lumen, and a second lumen for passage of a second medium, the second lumen including a bellows portion and a distal end of a construction sufficient for contact between a contact portion thereof and a selected portion of the tissue;
   providing means for expanding the first medium to form the second medium and selecting a longitudinal position of said expanding means;
   placing the contact portion in contact with the selected portion of the tissue; and
   expanding the first medium to form the second medium, whereupon the second medium is of a second temperature at the contact portion, the second temperature ranging from a temperature which is less than said first temperature to a temperature sufficient for cooling the tissue to form a lesion in the selected portion of the tissue.

103. A cryogenic method of treating biological tissue, comprising:
   providing at least two lumens, the at least two lumens comprising a first lumen for passage of a first medium, the first medium being pressurized and of a first temperature at a distal portion of the first lumen, and a second lumen for passage of a second medium, the second lumen including a bellows portion and a distal end of a construction sufficient for contact between a contact portion thereof and a selected portion of the tissue;
   providing means for expanding the first medium to form the second medium;
   placing the contact portion in contact with the selected portion of the tissue; and
   expanding the first medium to form the second medium, whereupon the second medium is of a second temperature at the contact portion, the second temperature ranging from a temperature which is less than said first temperature to a temperature sufficient for cooling the tissue to form a lesion in the selected portion of the tissue and being from about −70° C. to about −120° C.

104. The method of claim 102 and 103, wherein said placing comprises selecting a dimension of the bellows portion.

105. The method of claim 102 and 103, wherein said placing comprises selecting a shape of the bellows portion.

106. The method of claim 102 and 103, wherein said placing comprises guiding the contact portion to the selected portion.

107. The method of claim 102 and 103, further comprising sensing a temperature of the tissue.

108. The method of claim 102 and 103, further comprising sensing a temperature of the first medium or the second medium.

109. The method of claim 102 and 103, further comprising selecting a degree of cooling of the tissue.

110. The method of claim 109, wherein said selecting comprises selecting a pressure of the first medium or the second medium.

111. The method of claim 109, where said selecting comprises selecting a flow of the first medium or the second medium.

112. The method of claim 102 and 103 wherein said first medium is selected from a group consisting of R-23, R-503, R-13, R-508B, and any combination thereof.

113. The method of claim 102 and 103 wherein the tissue is affected with an undesirable condition.

114. The method of claim 102 and 103, wherein the tissue is organ tissue.

115. The method of claim 102 and 103, wherein the tissue is cardiopulmonary tissue.

116. The method of claim 115, further comprising stimulating electrical activity of the tissue.

117. The method of claim 115, further comprising recording electrical activity of the tissue.

118. The method of claim 115, wherein said second temperature is sufficient for cold-mapping the tissue.

119. The method of claim 115, wherein said second temperature is sufficient for forming a lesion sufficient to interrupt electrical conduction across the lesion.

120. The method of claim 102 and 103, wherein said second temperature is from about −20° C. to about −150° C.

121. The method of claim 102, wherein said second temperature is from about −70° C. to about −120° C.

122. The method of claim 102 and 103, wherein said providing at least two lumens comprises providing the first lumen and the second lumen in a heat-exchange relationship.

123. The method of claim 102 and 103, wherein said providing at least two lumens and said providing expanding means comprises providing the first lumen, the second lumen and the expanding means to form a closed media-flow pathway.

124. The method of claim 102 and 103, wherein said providing at least two lumens comprises providing a third lumen for passage of a third medium sufficient for cooling of the first medium.

125. The method of claim 124, wherein said providing at least two lumens comprises providing the first lumen and the third lumen in a heat-exchange relationship.

126. The method of claim 124, wherein said providing at least two lumens comprises providing the third lumen which forms a closed media-flow pathway.

127. The method of claim 124, wherein said providing the third lumen includes providing an expanding means for cooling said third medium.

128. The method of claim 124, wherein the first medium is selected from a group consisting of R-23, R-503, R-13, R-508B, and any combination thereof.

129. The method of claim 124, wherein the third medium is selected from a group consisting of halogenated hydrocarbon refrigerant mixtures, and any combination thereof.

130. A cryogenic method of treating cardiopulmonary tissue, comprising:
   providing at least two lumens, the at least two lumens comprising a first lumen for passage of a first medium, the first medium being pressurized and of a first temperature at a distal portion of the first lumen, and a second lumen for passage of a second medium, the second lumen including a bellows portion and a distal end of a construction sufficient for contact between a contact portion thereof and a selected portion of the tissue;

providing means for expanding the first medium to form the second medium;

placing the contact portion in contact with the selected portion of the tissue;

stimulating electrical activity of the tissue; and expanding the first medium to form the second medium, whereupon the second medium is of a second temperature at the contact portion, the second temperature ranging from a temperature which is less than said first temperature to a temperature sufficient for cooling the tissue to form a lesion in the selected portion of the tissue.

131. The method of claim 130, further comprising recording electrical activity of the tissue.

132. The method of claim 130, wherein said second temperature is sufficient for cold-mapping the tissue.

133. The method of claim 130, wherein said second temperature is sufficient for forming a lesion sufficient to interrupt electrical conduction across the lesion.

134. A cryogenic method of treating biological tissue, comprising:

providing at least two lumens, the at least two lumens comprising a first lumen for passage of a first medium, the first medium being pressurized and of a first temperature at a distal portion of the first lumen, a second lumen for passage of a second medium, the second lumen including a bellows portion and a distal end of a construction sufficient for contact between a contact portion thereof and a selected portion of the tissue, and a third lumen for passage of a third medium sufficient for cooling of the first medium;

providing means for expanding the first medium to form the second medium;

placing the contact portion in contact with the selected portion of the tissue; and expanding the first medium to form the second medium, whereupon the second medium is of a second temperature at the contact portion, the second temperature ranging from a temperature which is less than said first temperature to a temperature sufficient for cooling the tissue to form a lesion in the selected portion of the tissue.

135. The method of claim 134, wherein said providing at least two lumens comprises providing the first lumen and the third lumen in a heat-exchange relationship.

136. The method of claim 134, wherein said providing at least two lumens comprises providing the third lumen which forms a closed media-flow pathway.

137. The method of claim 134, wherein said providing the third lumen includes providing an expanding means for cooling said third medium.

138. The method of claim 134, wherein the first medium is selected from a group consisting of R-23, R-503, R-13, R-508B, and any combination thereof.

139. The method of claim 134, wherein the third medium is selected from a group consisting of halogenated hydrocarbon refrigerant mixtures, and any combination thereof.

* * * * *